(12) United States Patent
Takiguchi

(10) Patent No.: US 8,811,680 B2
(45) Date of Patent: Aug. 19, 2014

(54) COMPACT BIOMETRIC AUTHENTICATION DEVICE AND ASSOCIATED METHODOLOGY OF IMAGING AND DETECTING LIVING-TISSUE PATTERNS

(75) Inventor: Kiyoaki Takiguchi, Minato-ku (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/351,963

(22) Filed: Jan. 17, 2012

(65) Prior Publication Data
US 2012/0148143 A1 Jun. 14, 2012

Related U.S. Application Data

(63) Continuation of application No. 12/915,480, filed on Oct. 29, 2010, now Pat. No. 8,144,942, which is a continuation of application No. 12/015,263, filed on Jan. 16, 2008, now Pat. No. 7,869,624, which is a continuation of application No. 10/512,087, filed as application No. PCT/JP03/05696 on May 7, 2003.

(30) Foreign Application Priority Data

May 9, 2002 (JP) .................................. 2002-134534
May 9, 2002 (JP) .................................. 2002-134569

(51) Int. Cl.
*G06K 9/00* (2006.01)
*G01N 21/49* (2006.01)

(52) U.S. Cl.
CPC ..................................... *G01N 21/49* (2013.01)
USPC ........................................................ 382/115

(58) Field of Classification Search
CPC ...... A61B 5/14532; A61B 6/12; A61B 6/481; A61B 3/12; A61B 5/117; A61B 3/1233; A61B 5/1455; A61B 5/0261; A61B 5/0066; G06K 9/0012; G06K 9/00; G06K 9/00; G06K 9/003; G06K 9/00013; G06K 9/3216; G06K 9/00006; G06K 2009/00932; G06T 1/00; G06T 7/008; G06T 2207/300088; G06T 2207/30101; G06T 7/0012; B60R 25/04; G01N 21/65; G01N 21/49; G02B 26/001; G01J 3/26; G01J 3/44; G01P 3/366; G06F 3/021

USPC ........... 382/115, 127; 235/380; 340/5.1, 5.92; 704/246; 902/3, 4, 25
See application file for complete search history.

(56) References Cited

U.S. PATENT DOCUMENTS 4,699,149 A 10/1987 Rice
4,821,118 A 4/1989 Lafreniere
(Continued)

FOREIGN PATENT DOCUMENTS

DE 198 18 229 A1 10/1999
EP 0 359 554 A2 3/1990
(Continued)

OTHER PUBLICATIONS

Office Action issued Sep. 16, 2010, in Japan Patent Application No. 2008-265668.
(Continued)

*Primary Examiner* — Edward Park
(74) *Attorney, Agent, or Firm* — Oblon, Spivak, McClelland, Maier & Neustadt, L.L.P.

(57) ABSTRACT

The apparatus enables biometric authentication without the risk of forgery or the like and enables living-tissue discrimination. The roughness distribution pattern of deep-layer tissue of the skin covered with epidermal tissue is detected, thereby extracting a unique pattern of the living tissue. Biometric authentication is performed based upon the detected pattern. The roughness distribution pattern of the deep-layer tissue of the skin is optically detected using difference in optical properties between the epidermal tissue and the deep-layer tissue of the skin. Long-wavelength light, e.g., near-infrared light, is used as illumination light cast onto the skin tissue. A fork structure of a subcutaneous blood vessel is used as the portion which is to be detected, for example. The portion which is to be detected is determined based upon the structure of the fork structure. The living-tissue discrimination may be made using the subcutaneous blood vessel.

18 Claims, 11 Drawing Sheets

(56) References Cited

U.S. PATENT DOCUMENTS

| | | | |
|---|---|---|---|
| 5,077,803 A | 12/1991 | Kato et al. | |
| 5,228,449 A * | 7/1993 | Christ et al. | 600/504 |
| 5,297,554 A * | 3/1994 | Glynn et al. | 600/476 |
| 5,428,447 A * | 6/1995 | Toida | 356/601 |
| 5,719,950 A * | 2/1998 | Osten et al. | 382/115 |
| 5,736,734 A | 4/1998 | Marcus et al. | |
| 5,787,185 A | 7/1998 | Clayden | |
| 5,954,644 A * | 9/1999 | Dettling et al. | 600/322 |
| 5,994,702 A | 11/1999 | Clynne et al. | |
| 6,292,576 B1 | 9/2001 | Brownlee | |
| 6,296,610 B1 | 10/2001 | Schneider et al. | |
| 6,301,375 B1 | 10/2001 | Choi | |
| 6,349,227 B1 | 2/2002 | Numada | |
| 6,483,929 B1 | 11/2002 | Murakami et al. | |
| 6,668,071 B1 | 12/2003 | Minkin et al. | |
| 6,813,010 B2 | 11/2004 | Kono et al. | |
| 6,889,075 B2 | 5/2005 | Marchitto et al. | |
| 6,920,236 B2 | 7/2005 | Prokoski | |
| 6,983,061 B2 | 1/2006 | Ikegami et al. | |
| 6,993,160 B2 | 1/2006 | Miura et al. | |
| 7,228,166 B1 * | 6/2007 | Kawasaki et al. | 600/476 |
| 7,245,745 B2 | 7/2007 | Nagasaka et al. | |
| 7,415,139 B2 | 8/2008 | Takiguchi | |
| 2001/0021802 A1 | 9/2001 | Messerschmidt et al. | |
| 2001/0036297 A1 | 11/2001 | Ikegami et al. | |
| 2002/0009213 A1 | 1/2002 | Rowe et al. | |
| 2002/0016533 A1 | 2/2002 | Marchitto et al. | |
| 2002/0028004 A1 | 3/2002 | Miura et al. | |
| 2002/0048014 A1 | 4/2002 | Kono et al. | |
| 2002/0076089 A1 * | 6/2002 | Muramatsu et al. | 382/124 |
| 2002/0136435 A1 | 9/2002 | Prokoski | |
| 2003/0109772 A1 * | 6/2003 | Mills | 600/310 |
| 2004/0202354 A1 | 10/2004 | Togino | |
| 2005/0143662 A1 | 6/2005 | Marchitto et al. | |
| 2006/0095491 A1 | 5/2006 | Abe | |
| 2006/0177107 A1 | 8/2006 | Ishii | |

FOREIGN PATENT DOCUMENTS

| | | |
|---|---|---|
| JP | 07-021373 | 1/1995 |
| JP | 10-337282 A | 12/1998 |
| JP | 11-203452 | 7/1999 |
| JP | 2000-20684 | 1/2000 |
| JP | 2000-201907 | 7/2000 |
| JP | 2000-262496 | 9/2000 |
| JP | 2001-422 A | 1/2001 |
| JP | 2002-48507 | 2/2002 |
| WO | WO 92/09049 | 5/1992 |
| WO | WO 98/38907 A1 | 9/1998 |
| WO | 99/27848 | 6/1999 |
| WO | 00/75637 | 12/2000 |
| WO | WO 01/10296 A2 | 2/2001 |
| WO | WO 01/19252 * | 3/2001 |
| WO | 01/27882 | 4/2001 |
| WO | WO 01/54393 A2 | 7/2001 |

OTHER PUBLICATIONS

Office Action issued Feb. 25, 2011, in European Patent Application No. 09 163 990.6-2218.

Extended European Search Report issued Apr. 12, 2011, in European Patent Application No. 10176610.3-2218.

Sergio Fantini, et al., "Chapter 7 Frequency-Domain Techniques for Tissue Spectroscopy and Imaging", Handbook of Optical Biomedical Diagnostics, XP-002623993, Apr. 15, 2002, pp. 1-49.

Japanese Office Action issued Mar. 21, 2012 in patent application No. 2010-044762.

U.S. Office Action mailed Oct. 11, 2007 in co-pending U.S. Appl. No. 10/512,087.

European Office Action issued May 9, 2008 in patent application No. 03721050.7.

U.S. Office Action mailed Sep. 3, 2008 in U.S. Appl. No. 12/015,263.

U.S. Office Action mailed Feb. 27, 2009 in co-pending U.S. Appl. No. 10/512,087.

European Search Report issued Jul. 30, 2009 in patent application No. 09163990.6.

U.S. Office Action mailed Sep. 2, 2009 in U.S. Appl. No. 12/015,263.

U.S. Office Action mailed Sep. 16, 2009 in co-pending U.S. Appl. No. 10/512,087.

U.S. Office Action mailed Jul. 1, 2010 in U.S. Appl. No. 12/015,263.

U.S. Office Action mailed Dec. 23, 2010 in co-pending U.S. Appl. No. 10/512,087.

Japanese Office Action issued Sep. 11, 2008 in patent application No. 2002-134569 with English translation.

Japanese Office Action issued Jun. 26, 2012 in Patent Application No. 2010-044762 (1 of 2).

Japanese Office Action issued Jun. 26, 2012 in Patent Application No. 2010-044762 (2 of 2).

Japanese Office Action issued Jul. 24, 2012 in Patent Application No. 2011-219382.

Office Action issued Oct. 16, 2012, in Japanese Patent Application No. 2011-219382.

Communication pursuant to Article 94(3) EPC issued Jan. 27, 2014, in European Patent Application No. 10 176 610.3.

\* cited by examiner

COMPACT BIOMETRIC AUTHENTICATION DEVICE AND ASSOCIATED METHODOLOGY OF IMAGING AND DETECTING LIVING-TISSUE PATTERNS

CROSS REFERENCE TO RELATED APPLICATIONS

This application is a continuation of U.S. application Ser. No. 12/915,480 filed Oct. 29, 2010, which is a continuation of U.S. application Ser. No. 12/015,263 filed Jan. 16, 2008, which is a continuation of U.S. application Ser. No. 10/512,087 filed on Apr. 7, 2005, which is a National Stage of PCT/JP03/05696, filed on May 7, 2003, all of which claim priority to Japanese Patent Application No. 2002-134569, filed May 9, 2002 and Japanese Patent Application No. 2002-134534, filed May 9, 2002. The contents of each of these documents are incorporated herein by reference.

TECHNICAL FIELD

The present invention relates to a new biometric pattern detecting method and biometric pattern detecting device for acquiring the pattern of a deep skin layer such as dermis or the like, and particularly to a biometric authentication method and a biometric authentication device.

BACKGROUND ART

Fingerprints, palm patterns, or the like, are widely used for person authentication. These patterns are skin ridge patterns wherein a part of the epidermal tissue is embedded in the roughness structure of the dermis, and accordingly, the patterns can be directly observed from the outside. That is to say, the aforementioned pattern essentially corresponds to the deep layer structure of the skin such as dermis or the like. The skin of the portion such as a palm, a sole, or the like, has a special structure wherein the epidermal structure corresponds to the structure of the dermis beneath the epidermal tissue, unlike the skin of other portions, leading to the physiological advantages such as high sensitivity of the touch sensory nerves of which ends are positioned in the deep layer of the skin to external stimulation, great toughness regarding friction, and so forth. Conventionally, the fingerprints have been used for person authentication since the fingerprints exhibit sufficient stability essentially due to the high stability of the deep layer structure therebeneath.

However, the aforementioned biometric authentication using the fingerprints does not provide sufficient security against so-called "spoofing" or the like. That is to say, the fingerprints are readily left on various objects, and the fingerprints left on the object can be easily observed, leading to a risk that other persons would forge the fingerprints.

On the other hand, it is expected that biometric authentication using the epidermal tissue of other portions avoids the aforementioned risk of forgery, for example. However, the epidermal tissue changes due to metabolism thereof in a 28-day cycle. Furthermore, the epidermal tissue readily exhibits various conditions due to rough skin, dry skin, or the like. Accordingly, the epidermal tissue of other portions does not have sufficient stability. Furthermore, it has become clear from measurement that the patterns of the epidermal tissue of the base portion of a finger, the thenar region, and the like, do not correspond to the patterns thereunderneath at all, rather, in some cases, the patterns of the epidermal tissue thereof are formed orthogonal to the patterns thereunderneath, except for a special case such as the fingerprints, leading to difficulty in biometric authentication using such a portion.

That is to say, a large part of the epidermal tissue of the human body, including the palm portion such as the thenar region and so forth, the base portion of a finger, the skin of the back of the hand, and the like, has patterns different from the patterns of the deep-layer structure therebeneath, except for a special case such as the fingerprints which are fingertip impressions, wherein the epidermal tissue directly corresponds to the deep-layer structure, allowing external observation thereof. Furthermore, it is difficult to make external observation of the deep-layer structure therebeneath due to scattering of visible light from the 6-layer epithelial structure and absorption thereof by the melanin pigment in basal cells or the like. This leads to difficulty in development of a finger-ring-type authentication device wherein person authentication is performed using the pattern of the skin in contact with the inner face of the finger ring at the time of being fit by the user.

On the other hand, the deep-layer structure beneath the epidermal tissue is essentially unique to an individual, and exhibits sufficient stability over time, as with a well-known example of fingerprints or the like. Note that a tattoo wherein a pigment is injected into the deep-layer structure, and a stretch mark caused by pregnancy, also have the same stability due to the properties of the deep-layer structure beneath the epithelium tissue. Accordingly, it is expected that the pattern beneath the epithelium tissue, i.e., the deep-layer structure of the epithelium tissue is suitably used for biometric authentication. However, the aforementioned patterns cannot be directly observed, neither left on an object by contact with the object, and accordingly, development of the authentication device using the pattern of the deep-layer structure has not been made, although the pattern of the deep-layer structure has the same performance of biometric authentication as with fingerprints.

The present invention has been made in order to solve the aforementioned problems, and accordingly, it is an object thereof to provide a biometric pattern detecting method and biometric pattern detecting device for acquiring the roughness structure distribution of the deep-layer structure beneath the epithelium tissue (patterns beneath the epithelium tissue) or the blood-vessel pattern beneath the epithelium tissue, which cannot be directly observed. Furthermore, it is an object of the present invention to provide a biometric authentication method and a biometric authentication device which enables stable biometric authentication while preventing a risk of "spoofing", e.g., forgery or the like.

DISCLOSURE OF INVENTION

The present inventor has made various studies in order to achieve the aforementioned object. As a result, it has become clear that discrimination can be made between epidermal tissue and deep-layer tissue of the skin using difference in properties (optical properties, electric properties, and temperature difference) therebetween, and the roughness distribution pattern of the deep-layer tissue of the skin wherein visual observation is difficult due to shielding with epidermis is clearly detected. Accordingly, it has become clear that the pattern of any desired portion of the skin and subcutaneous tissue over the entire body of the user can be detected, as well as a special portion where the epidermal pattern corresponds to the dermal pattern such as fingerprints or the like, and the pattern thus detected can be applied to biometric authentication (person authentication).

The present invention has been made based upon the information thus obtained. That is to say, with a living-tissue pattern detecting method according to the present invention, the roughness distribution pattern of the deep-layer tissue of the skin covered with the epidermal tissue is detected using difference in properties (optical properties, electric properties, and temperature difference) therebetween, thereby extracting a unique pattern of the living tissue. Furthermore, a living-tissue pattern detecting device according to the present invention includes means for detecting the roughness distribution pattern of the deep-layer tissue of the skin covered with the epidermal tissue. Furthermore, with a biometric authentication method according to the present invention, the roughness distribution pattern of the deep-layer tissue of the skin covered with the epidermal tissue is detected so as to be compared to a pattern registered beforehand, whereby biometric authentication is performed. Furthermore, a biometric authentication device according to the present invention includes means for detecting the roughness distribution pattern of the deep-layer tissue of the skin covered with the epidermal tissue, and the pattern thus detected is compared to a pattern registered beforehand, whereby biometric authentication is performed.

The present invention has been made based upon the basic concept that authentication is performed not using an epidermal pattern, but using the pattern of the deep-layer tissue of the skin, e.g., a dermal pattern. The roughness distribution pattern (pattern) of the deep-layer tissue is unique to individual living tissue as with fingerprints, palm pattern, sole pattern, and so forth, and exhibits small change over time, i.e., exhibits high stability. Furthermore, the deep-layer tissue of a large part of the skin has a different pattern from that of the epidermal layer, except for special portions such as a fingertip having fingerprints which can be observed from the outside, or the like. Furthermore, the pattern of the deep-layer tissue is covered with the epidermal tissue, leading to difficulty in visual observation from the outside. Furthermore, no impression is left on any object even if the tissue comes in contact with the object. Accordingly, it is almost impossible for other persons to forge such a pattern.

Furthermore, with the present invention, the system does not detect the structure of dead tissue having no nucleus such as the horny layer of the skin, specifically, fingerprints, and so forth, but detects deep-layer tissue of the skin which is living tissue, as described above. The deep-layer tissue of the skin does not maintain the pattern thereof if the deep-layer tissue is cut off from the living human body. For example, the deep-layer tissue of the skin has blood capillaries therein, and the pattern formed of the blood flow within the blood capillaries is unique to the living tissue. Furthermore, if the tissue is cut off from the living human body, the aforementioned pattern is immediately lost due to contraction of blood vessels, retention of blood, lost of blood, and so forth. This affects the pattern of the entire deep-layer tissue of the skin. Thus, with the present invention, the biometric authentication and the living-tissue discrimination are integrated, thereby suppressing the risk of "spoofing" using the tissue of the user to an unrealistic level, and thereby realizing true "biometric authentication".

The aforementioned deep-layer tissue of the skin, e.g., the roughness distribution pattern of dermal layer can be optically detected using the fact that difference in the structure between epidermal tissue formed of simple cells or dead cells thereof and dermal tissue which is dense connective tissue causes difference in scattering properties and refraction properties therebetween, and this leads to depolarization or difference in frequency between the incident light and the returning light.

Specifically, first, polarized light is cast onto the tissue, as well as detecting the reflected light through a polarizing filter with the polarizing plane orthogonal to that of the aforementioned polarized light, thereby detecting the aforementioned roughness distribution pattern. In this case, the polarized light is cast on the surface of the tissue, and the reflected light is filtered with the polarizing filter with the polarizing plane orthogonal to the aforementioned polarized light, and accordingly, only the depolarized light due to scattering in the living tissue, such as back-scattered light, light split due to birefringence, and so forth, is detected, thereby extracting the pattern of the tissue having the nature which causes scattering of light, such as a dermal layer beneath epidermis and so forth. In particular, an arrangement may be made wherein long-wavelength light such as near-infrared light and so forth, which has the nature that the light readily passes through the epidermal tissue, and is readily scattered in dermal tissue, is employed as the aforementioned polarized light, thereby reducing adverse effects due to absorption of the polarized light in the living tissue, and thereby effectively detecting the pattern of the subcutaneous tissue beneath epidermis due to desirable optical properties (scattering properties, birefringence properties, and so forth) of the subcutaneous tissue beneath epidermis.

Second, an arrangement may be made wherein the illumination light is case onto the tissue, as well as causing interference between a part of the illumination light and the reflected light so as to detect change in wavelength components of the reflected light in the form of an interference pattern, thereby extracting a unique pattern of the living tissue. In this case, the system causes interference between the reflected or scattered light from the skin and the incident light split by a half mirror or the like serving as reference light, thereby detecting change in wavelength components due to birefringence or scattering in the internal structure of the skin in the form of a beat pattern (interference pattern). Such a beat pattern has properties unique to an individual living tissue, thereby enabling authentication using the beat pattern.

Furthermore, with the biometric authentication method and the biometric authentication device according to the present invention, an arrangement may be made wherein the subcutaneous tissue structure covered with epidermal tissue is electrically detected using difference in electric properties between the epidermal tissue and the deep-layer tissue of the skin, and the subcutaneous tissue structure thus detected is compared to a pattern registered beforehand, thereby enabling biometric authentication. Furthermore, an arrangement may be made wherein the subcutaneous tissue structure covered with epidermal tissue is detected using difference in temperature between the epidermal tissue and the deep-layer tissue of the skin, and the subcutaneous tissue structure thus detected is compared to a pattern registered beforehand, thereby enabling biometric authentication.

DETAILED DESCRIPTION OF THE PREFERRED EMBODIMENTS

Figure 1:
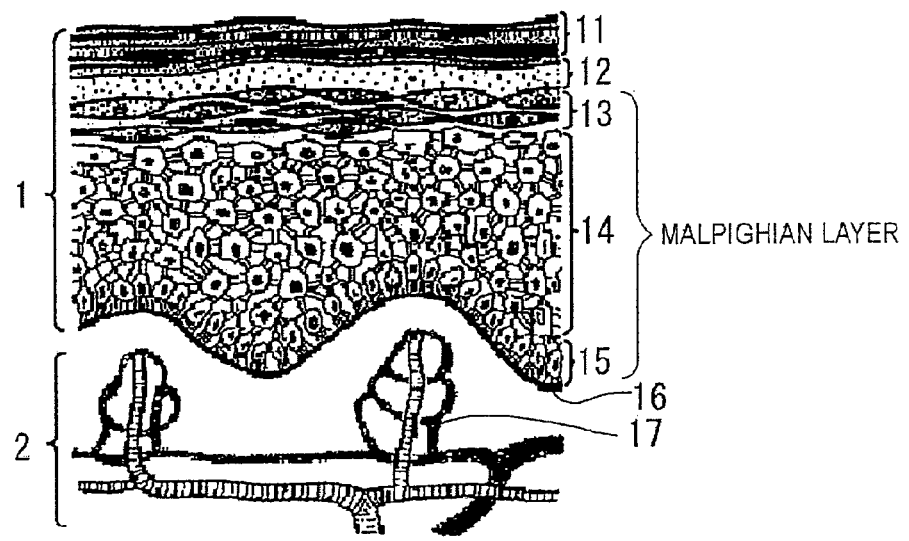
FIG. 1 is a schematic diagram which shows skin tissue.

Detailed description will be made below regarding a biometric pattern detecting method, a biometric pattern detecting device, a biometric authentication method, and a biometric authentication device, according to the present invention with reference to the drawings.

For example, the biometric authentication using the fingerprints has a risk of forgery by other persons since the impressions (fingerprints) are readily left on another object, and can be easily observed. As a countermeasure, there is the need to perform living-tissue discrimination for determining whether or not the detected fingerprints have been acquired from the live tissue without unauthorized means. The reason is that the biometric authentication using the fingerprints is essentially measurement wherein the tissue structure of the dead tissue having no nucleus such as the horny layer of the skin is optically or electrically detected.

The security performance of the biometric authentication using the aforementioned fingerprints, the iris, or the like, does not only depend upon the detection precision, but also the aforementioned living-tissue discrimination. For example, let us say that other persons can breach the living-tissue discrimination at the time of the biometric authentication using the fingerprints, as well as having obtained the tissue used for the biometric authentication. This allows the other persons to easily make "spoofing", resulting in deterioration in the security of the system to zero. Furthermore, the aforementioned "spoofing" using the tissue leads to a new additional risk of a serious hazard to the body and the life of the user, as well as the financial risk in a case wherein
the security of the conventional credit card is breached. The aforementioned serious hazard to the body and the life of the user will be referred to as "surgical hazard" hereafter.

The biometric authentication needs to provide not only the sufficient limitation security performance which has been proposed in the conventional authentication techniques, but also the sufficient security performance against the surgical hazard for securing the safety of the user, which has been hardly proposed in the conventional techniques.

That is to say, the security performance of the biometric authentication consists of two kinds of the security performance. One security performance depends upon the precision of the "authentication" for identifying whether or not that the tissue which is to be authenticated matches the tissue of the user. The other security performance depends upon the precision of the "living-tissue discrimination" for determining whether or not the tissue used for authentication is live tissue, i.e., for confirming that the tissue is not dead tissue cut off from the body of the user. The conventional biometric authentication techniques have provided only the precision and reliability of the former security performance. In this case, the "biometric authentication" used here essentially means authentication without "living-tissue discrimination", and accordingly, does not mean true biometric authentication. Accordingly, from the practical perspective, the conventional security system having such a problem may lead to the additional hazard, i.e., the surgical hazard.

With the simplest spoofing method without any particular technique and equipment, spoofing is made using the tissue such as a finger, arm, eyeball, or the like, which has been cut off from the body of the user. Such a simple method for breaching the biometric authentication security leads to a new additional and serious hazard to the life and body of the user, of which money cannot replace, even in a case of small finance loss. Accordingly, the conventional biometric authentication methods using the fingerprints, iris within the eyeball, or the like, remain accessory means used with other main authentication means, or remain accessory means in a limited form for unimportant matter, or the like. This leads to difficulty in wide use of the conventional biometric authentication.

On the other hand, forgery of the fingerprints or the like can be relatively easily made. As a countermeasure against forgery of the fingerprints, electrostatic capacity or electrostatic induction is measured between the finger and the electrode so as to detect the distance between the surface of the skin and the electrode, thereby detecting the pattern of the fingerprints, using the fact that the surface of the skin serves as a conductive material due to moisture (water) containing salt from sweat or the like secreted from the live tissue. This is a kind of an example of the biometric authentication with the "living-tissue discrimination". The reason is that the aforementioned measurement is impossible without moisture which is an electrolyte containing salt from sweat or the like secreted from the live tissue.

However, while the aforementioned detecting method requires moisture serving as an electrolyte on the surface of the object which is to be authenticated, the aforementioned object does not need to be alive. That is to say, with the aforementioned detecting method, the "living-tissue discrimination" is not performed for confirming that the object which is to be authenticated has not been cut off from the body of the user, for example. Accordingly, with the aforementioned detecting method, it is difficult to reject unauthorized means such as forgery of the fingerprints formed of a gel material having water retentivity, or the finger which has been cut off from the body of the user and subjected to spraying with or soaking in a physiological salt solution.

Furthermore, with the biometric authentication using DNA or the like, while forgery of the DNA is difficult, it is essentially impossible to discriminate whether the DNA sample which is to be authenticated belongs to the live body of the user or is formed of DNA mass-produced by replicating the DNA obtained from the dead body or a hair of the user with the PCR (Polymerase Chain Reaction). Accordingly, the biometric authentication using DNA does not include "living-tissue discrimination". Accordingly, the biometric authentication using DNA needs some sort of a countermeasure such as a new separate sensor for discriminating whether or not the sample belongs to the live body of the user with a suitable method such as detection of the blood flow in the finger using infrared light and so forth, as well as "biometric authentication".

In this case, the "biometric authentication" is performed by two means. One is "authentication", and the other is "living-tissue discrimination". That is to say, the conventional "biometric authentication" does not only depend upon the "authentication" serving as a "front door" as if it were, but also "living-tissue discrimination" serving as a "back door" as if it were, which is performed in separate detection means using a different physical principle. Accordingly, the conventional "biometric authentication" has a problem that if other persons breach the security of the "living-tissue discrimination" serving as a back door, the security of the biometric authentication security is breached, leading to a risk of "spoofing", and further leading to a risk of surgical hazard. With the "living-tissue discrimination", the system discriminates whether the tissue which is to be authenticated is alive or dead. However, the living tissue has great diversity, and accordingly, the "living-tissue discrimination" must be performed for a single tissue sample with a sufficiently wide threshold range, as can be understood from the standing theory (central dogma) what life is. This leads to an essential problem of the poor security of the conventional "biometric authentication" against "spoofing". That is to say, with the conventional "biometric authentication" having separate means formed of the means of "authentication" and the means of "living-tissue discrimination", other persons can easily find and analyze the discrimination mechanism for discriminating whether the tissue is alive or dead. Accordingly, there is demand for the "true" biometric authentication integrating the means of "authentication" and the means of "living-tissue discrimination", i.e., the biometric authentication without the aforementioned "back door".

With the present invention, biometric authentication is performed based upon the detected roughness distribution pattern of the epithelial deep-structure tissue, e.g., dermal layer, instead of patterns of the epidermal tissue such as fingerprints described above.

FIG. 1 is a schematic diagram which shows skin tissue which is roughly classified into epidermis 1 and dermis 2. The epidermis 1 is keratinized stratified flattened epithelium formed of a horny layer 11, a lucid layer 12, a granular layer 13, a prickle layer 14, a basal layer 15, and a basement membrane 16. Note that a layer formed of the granular layer 13, the prickle layer 14, a basal layer 15, is referred to as "Malpighian layer".

The horny layer 11 has a lamellar liquid crystal structure formed of a bilayer membrane formed of a horny-layer intercellular lipid. The lucid layer 12 has a cholesteric liquid crystal structure, and the granular layer 13 is formed of cells of which cytoplasm contains basic structures which are referred to as "keratohyalin granule" having optical properties which cause reflection and scattering of light, like beads. On the other hand, the basal layer 15 has melanin granules. As described above, the skin tissue has a multi-layer structure having various optical scattering/absorption properties due to each layer, leading to the advantage of preventing the living tissue from exposure to ultraviolet light or the like. In particular, the epidermis 1 has a kind of dichroic properties for ultraviolet light due to the multi-layer structure formed of thin membranes each of which has a different refractive index. However, the epidermis 1 is translucent tissue having relatively high scattering properties in a range of visible light, except for absorption of the light due to the melanin pigment. Note that the epidermis 1 has high transparency in a longer wavelength range than with red visible light or near-infrared light. Accordingly, the light reflected from the blood flow in the blood capillaries within the dermis 2 beneath the epidermis 1 is scattered. The scattered light is observed as a complexion or the color of the skin. Note that the color of the skin essentially depends upon the distribution of the melanin pigment and the blood flow within the blood capillaries in the dermis 2. The flow of an electrolyte fluid such as blood or lymph does not occur in the epidermis 1, and accordingly, the epidermis 1 essentially serves as a dielectric as exemplified by the horny layer 11.

On the other hand, the dermis 2 has essentially different structure as compared with the epidermis 1. The dermis 2 essentially comprises the dense fibrous connective tissue formed of collagen or elastin, and a blood capillary pattern, unlike the epidermis 1 formed of simple cells having no blood capillaries.

The dermis 2 is classified into a papillary layer and a reticular layer. The dermal papillary layer is in contact with the epidermal tissue through the basement membrane serving as the lowermost layer of the epidermal tissue, is formed of the connective tissue and the blood capillary pattern, and has the end of the sensory nerve. The reticular layer is formed of collagen having an array structure, elastin for connecting the collagen structures one to another, and a matrix which fills the space therebetween. The dermis 2 contains a great amount of the electrolyte fluid due to great amount of blood capillaries and the flow of lymph or the like, leading to extremely high electric conductivity as compared with the epidermis 1.

[Method Using the Optical Properties]

While the collagen and elastic fibrous tissue forming connecting tissue of the dermis 2 exhibits high optical birefringence, the epidermal tissue does not exhibit birefringence. On the other hand, the epidermis 1 has optical properties which cause scattering of light, and polarization properties which cause depolarization of light due to scattering thereof. In a basic mechanism, the tissue exhibits a unique vertical/horizontal polarization ratio dependent upon the size and shape of the scattering particles therewithin.

In a case wherein the wavelength of the electromagnetic wave is far greater than the particle size, Rayleigh scattering occurs.

In a case wherein the wavelength of electromagnetic wave generally matches the particle size, Mie scattering occurs. (which causes the color of cloud particles, aerosol, and cumulonimbus, to appear white)

In a case wherein the wavelength of electromagnetic wave is far smaller than the particle size, the electromagnetic wave geometrically passes through the object. (e.g., rainbow formed of rain particles, diamond dusts)

The dermis 2 having a thickness greater than a certain thickness appears white, like milk agar. Furthermore, the dermis 2 has optical properties wherein the longer the wavelength of light is, the more readily the light passes through the dermis 2. On the other hand, the shorter the wavelength of the light is, the more readily the light is scattered. Let us say that the dermis 2 contains a significant amount of absorption pigment. In this case, the short-wavelength light scattered at a shallow portion returns to the eyes of the observer with a high probability. However, the long-wavelength light returns to the observer with a low probability due to absorption of the light in the pigment. Accordingly, the blood capillaries at the shallow portion of the skin appear vivid red from external observation, and the vein and hemangioma positioned at relatively deep portion appears relatively blue. Note that while the nevus (birthmark) due to melanocyte, which is positioned at the boundary between the dermis and the epidermis appears relatively brown from the external observation, the blue nevus positioned in the dermis appears relatively blue from the external observation, wherein the name agrees with the color. Furthermore, the Ota's nevus and Mongolian spot due to dermal melanocyte appear relatively blue from the clinical observation.

With the present invention, the system detects the roughness distribution pattern or the like of the deep structure of the skin (e.g., dermal tissue) using difference in optical properties or electric properties between the dermal tissue and the epidermal tissue, whereby biometric authentication is performed. For example, the reflected light from the tissue sample is subjected to filtering so as to discriminate the dermal layer formed of the connecting tissue, collagen fibrous tissue, or the like, in a deeper portion, from the epidermal tissue, using the difference in the scattering/polarization properties of the reflected light as to the incident white light between the dermal tissue and the epidermal tissue. This enables the user to clearly discriminate the dermal tissue wherein observation is difficult due to shading by the epidermal tissue, from the epidermal tissue. In particular, the present invention has the advantage of enabling person authentication by detecting the pattern of the dermal tissue, even using the skin or the subcutaneous tissue of any portion of the body of the use, as well as a special portion such as fingerprints and so forth, where the dermal tissue pattern matches the epidermal tissue pattern.

Figure 2:
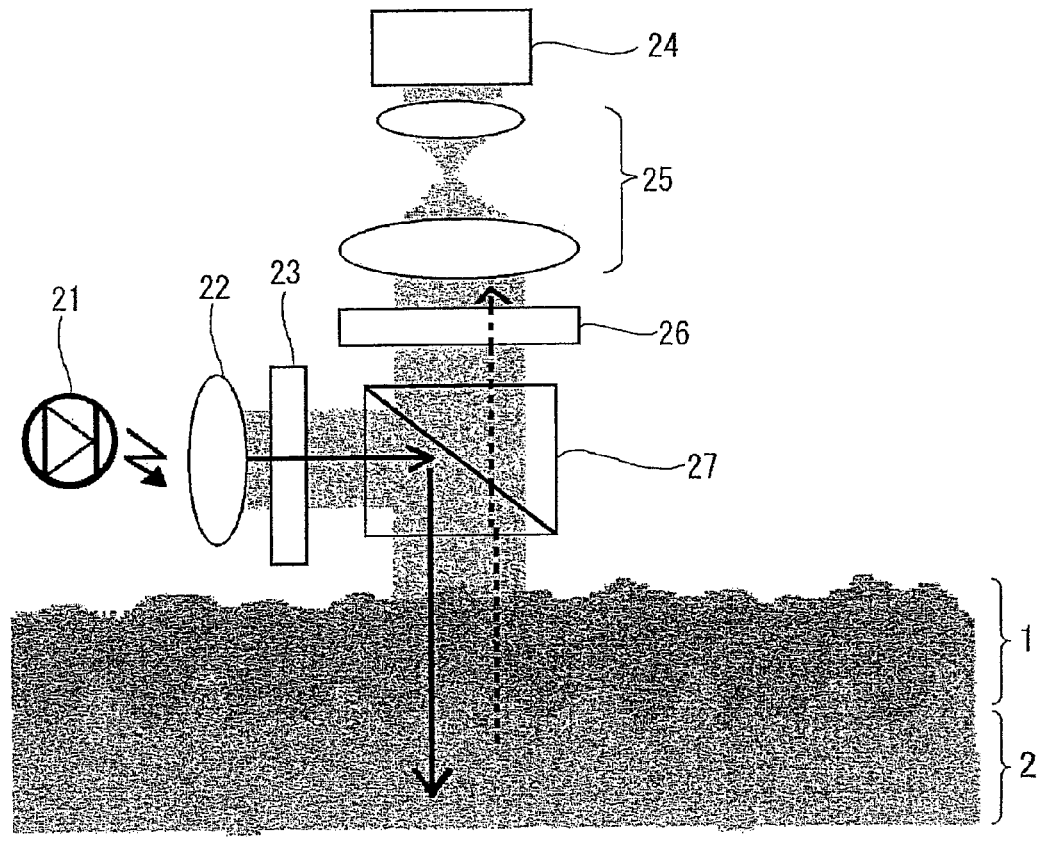
FIG. 2 is a schematic diagram which shows an example of a detecting device (authentication device) for acquiring an image of dermal tissue using depolarization due to back-scattering of light.

FIG. 2 shows a configuration example of a detecting device for acquiring an optical image of the dermis 2 beneath the epidermis having a great diversity of scattering mechanisms as described above. The detecting device has a configuration which allows the light returning due to scattering and birefringence to pass through the receiver of the detecting device while preventing the light reflected from the epidermal layer from being received, by polarizing means including polarizing plates at the light-emitting unit and the light-receiving unit with planes of polarization orthogonal one to another.

Description will be made below regarding a specific configuration. First, an illuminating optical system includes a light source 21, optical lens 22, and an illumination-unit polarizing plate 23. Any suitable light source such as an LED or the like can be employed as the light source 21. Note that a light source for emitting long-wavelength light such as near-infrared light or the like is preferably employed as the light source 21 since such long-wavelength light has the nature to readily pass through the epidermal tissue, as well as being reflected by the dermal tissue. Such a configuration enables acquisition of the pattern of the tissue using the optical properties such as scattering properties, birefringence properties, and so forth.

On the other hand, an imaging optical system includes an imaging device (solid-state image sensor, e.g., CCD) 24 serving as a light-receiving device, an imaging lens set 25, and a receiving-unit polarizing plate 26. Furthermore, a half mirror 27 is disposed on a light path between the aforementioned illuminating optical system and the imaging optical system. Note that the aforementioned illuminating optical system and the imaging optical system are disposed with the polarizing planes orthogonal one to another.

With the aforementioned detecting device, the illumination light is cast from the light source 21 onto the skin with a single polarizing plane determined by the illumination-unit polarizing plate 23. On the other hand, the imaging optical system includes the receiving-unit polarizing plate 26 with the polarizing plane orthogonal to that of the illumination-unit polarizing plate 23. Accordingly, the reflected light from the epidermal tissue through simple reflection passes through with a polarizing plane orthogonal to the polarizing plane of the receiving-unit polarizing plate 26, whereby such reflected light is intercepted by the receiving-unit polarizing plate 26.

The illumination light cast onto the skin from the illumination optical system reaches the deep-layer tissue of the skin (e.g., dermal tissue), leading to scattering of the light or birefringence thereof due to various kinds of tissue, resulting in depolarization thereof. The reflected light, e.g., back-scattered light, passes through the half mirror 27, and is introduced to the aforementioned imaging optical system. In this case, depolarization has occurred for the reflected light, thereby allowing the reflected light to pass through the receiving-unit polarizing plate 26, whereby the back-scattered light reaches the imaging device 24.

The aforementioned scattered or reflected light exhibits phase shift as to the incident light due to birefringence thereof caused by reflection or scattering in the dermal tissue containing connecting tissue, collagen, and so forth, having properties which cause birefringence of the light. Note that the epidermal tissue does not contain the aforementioned materials having properties which cause birefringence of the light. With the present embodiment, the system discriminates between the scattered/reflected light from the epidermal tissue and from the dermal tissue (which causes birefringence of the light) by detecting the difference in the phase of the light therebetween.

Furthermore, an arrangement may be made wherein the system allows only the reflected light with a phase shift in a predetermined wavelength range due to birefringence in the dermal tissue, to pass through a band-pass filter such as a dichroic filter or the like, and detects only the light thus selected, thereby selectively detecting only the tissue which causes birefringence of the light, and thereby enabling external observation of the dermal tissue in a noninvasive manner.

On the other hand, as an example of measurement of the skin using the polarizing light, a method is known in the field of the beauty industry, wherein the skin is observed with polarized light using the optical properties of a polarizing filter in a range of the visible light. For example, a measurement method for evaluating the surface of the skin is known, wherein the beauty factors such as the glossiness of the skin, the brightness thereof, and so forth, are measured (see Japanese Examined Patent Application Publication No. 3,194, 152, or Japanese Examined Utility Model Registration Application No. 7-22655).

However, such conventional measurement methods are not configured in order to observe the tissue beneath the epidermis, such as the dermal tissue or the like, but are configured in order to evaluate the surface of the skin using visible light from the perspective of beauty and appearance. That is to say, the disclosed arrangement is nothing but a method wherein an image of the skin is obtained from scattered light from the skin using visible light while preventing deterioration in image quality due to the excessive brightness of the reflected light directly reflected from the horny layer of the epidermis or the like, using the well-known nature that depolarization of the light occurs due to scattering, thereby obtaining a stable image of the skin.

While such conventional methods using visible light have a function of detecting the scattered light from the epidermis, use of the visible light leads to difficulty in precise detection of the state of the dermal layer due to absorption or interception of the visible light by the prickle cells or basal cells containing melanin pigment. Furthermore, this leads to difficulty in forming an image by extracting light wherein birefringence thereof has occurs due to the dermal tissue. No method has yet been proposed whatsoever wherein the structure of the dermal tissue is observed using the fact that the dermal layer containing the connective tissue, the collagen tissue, and so forth, exhibits great anisotropic optical properties which cause birefringence of the light as compared with the epidermis, and the fact that the epidermal tissue exhibits high transmissivity of near-infrared light, unlike visible light, i.e., using the scattering properties and the birefringence properties of the dense connective tissue forming the dermal tissue; this is being newly proposed in the present specification.

Figure 3:
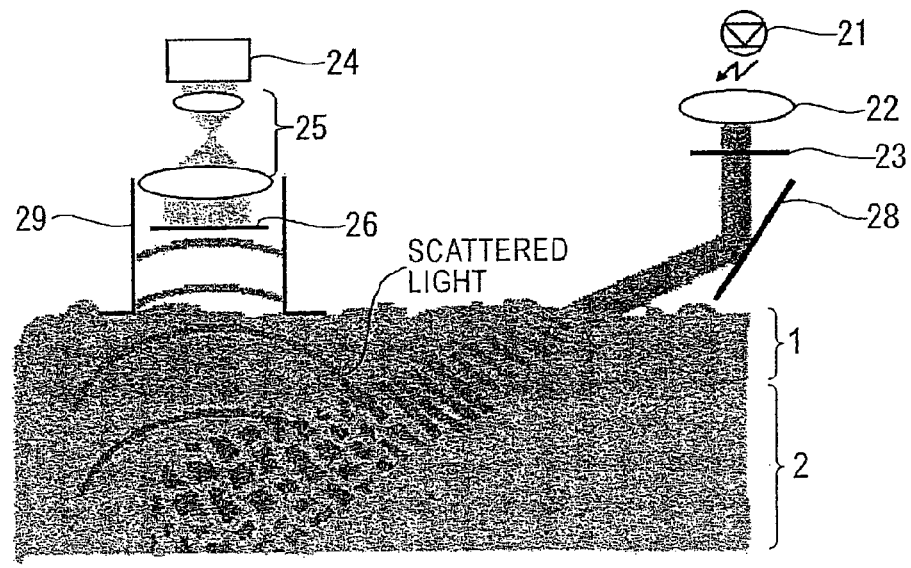
FIG. 3 is a schematic diagram which shows an example of a detecting device (authentication device) for taking an image of scattering light from the skin at a desired depth.

As described above, the aforementioned detecting device has a function for detecting the dermal-layer structure (e.g., the roughness distribution pattern) using the scattering properties or the birefringence properties of the dense connective tissue forming the dermal layer. Note that the detecting device having a configuration as shown in FIG. 2 has the disadvantage of reduction of the SN ratio due to increased noise due to scattered light from the epidermal layer, and scattered light from the dermal tissue, subcutaneous tissue, and so forth, beneath the surface of the dermal layer which is to be detected. FIG. 3 shows an effective configuration example of the detecting device for solving the aforementioned problem, wherein the illumination light is cast onto the skin with a shallow angle, as well as limiting the aperture of the imaging optical system.

The detecting device shown in FIG. 3 further includes a moving reflecting mirror 28, and has a configuration wherein the illumination is cast onto the skin in a slant direction from the illumination optical system. Furthermore, the detecting device includes the imaging optical system disposed just above the tissue which is to be measured, thereby enabling direct detection of the back-scattered light and side-scattered light without the half mirror 27. Furthermore, the detecting device includes a shield 29 for limiting the aperture, thereby allowing only the light returning from the portion just underneath the aperture, to reach the imaging device 24.

With the detecting device having such a configuration, the illumination light cast from the illumination optical system passes through the tissue toward the deep-layer structure of the skin (dermal layer) from the epidermal layer in a slant direction. In this case, scattering of light due to an excessively shallow portion, i.e., the epidermal tissue, occurs in the region on the right side shown in the drawing, thereby preventing the scattered light from the excessively shallow portion from reaching the imaging optical system with the aperture limited by the shield 29. In the same way, scattering of light due to an excessively deep portion occurs in the region on the left side shown in the drawing, thereby preventing the scattered light from the excessively deep portion from reaching the imaging optical system with the aperture limited by the shield 29. On the other hand, with the detecting device wherein the angle of the aforementioned moving reflecting mirror 28 is adjusted such that the position of the dermal tissue onto which the incident light is cast, is positioned just underneath the aforementioned imaging optical system, only the scattered light from this region (dermal tissue) reaches the imaging optical system.

Next, description will be made regarding a detecting method using the birefringence of the dermal tissue. First, an arrangement may be made using a well-known method for detecting the birefringence, e.g., using the optical heterodyne interferometry for converting the phase difference between the illumination light and the reflected light or transmitted light into the phase difference in the beat signals, instead of a method using a band-pass filter as described above.

Figure 4:
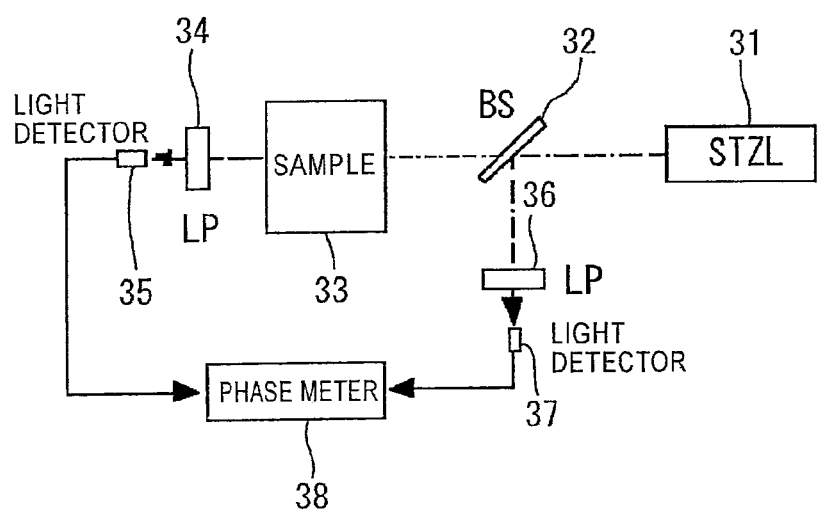
FIG. 4 is a schematic diagram for describing a mechanism of birefringence measurement with the optical heterodyne interferometry.

FIG. 4 is a diagram which shows a mechanism of such an arrangement. The detecting device has a configuration wherein the oscillating light is cast to a sample 33 from a light source, e.g., a Stabilized Transverse Zeeman Laser (STZL) 31 through a half mirror 32, and the transmitted light (signal light) passing through a polarizing plate 34 is detected with a photo-detector 35. At the same time, a part of the oscillating light emitted from the Stabilized Transverse Zeeman Laser 31 is reflected by the half mirror 32, following which the reflected light (reference light) passes through a polarizing plate 36, whereby the reference light is detected with a photo-detector 37. Then, the phase difference in the light detected by the aforementioned photo-detectors 35 and 37 is measured with an electronic phase meter 38.

Here, the linear polarizers (polarizing plates 34 and 36) are used for causing interference between two light waves. Note that this mechanism enables measurement of the birefringence of the light with precision determined by the electronic phase meter 38. In general, the electronic phase meter 38 exhibits the measurement precision of 0.1 degree (or more), thereby enabling measurement of the birefringence of the light with high precision of approximately 1/4000 of the wavelength of the light.

Description will be made below regarding a mechanism of the optical heterodyne interferometry. First, the electric-field component of the reference light Er and the electric-field component of the signal light Es are represented as follows.

$$E_r = a_r \cos(2\pi f_r t + \phi_r) \tag{1}$$

$$E_s = a_s \cos(2\pi f_s t + \phi_s) \tag{2}$$

Here, $a_r$ and $a_s$ represent the amplitude of the reference light and the amplitude of the signal light, respectively. In the same way, $f_r$ and $f_s$ represent the frequency of the reference light and the frequency of the signal light, respectively, and $\phi_r$ and $\phi_s$ represent the phase of the reference light and the phase of the signal light, respectively.

In general, the light intensity I is represented by the square of the electric-field component, and accordingly, the light intensity I obtained by superimposing the two light waves is represented as follows.

$$\begin{aligned} I &= \langle |E_s + E_r|^2 \rangle \\ &= \frac{a_s^2 + a_r^2}{2} + 2a_s a_r \cos(2\pi (f_s - f_r) \cdot t + (\phi_s - \phi_r)) \\ &= \frac{a_s^2 + a_r^2}{2} + 2a_s a_r \cos(2\pi f_b t + \Delta) \end{aligned} \tag{3}$$

Note that in the above expression, the reference symbol "< >" represents the average over time. On the other hand, $f_b$ ($=f_s-f_r$) represents the optical-beat frequency, and the reference character "Δ" ($=\phi_s-\phi_r$) represents the phase difference between two light components.

The photoelectric current detected with the photo-detector is classified into the DC component represented by the first term and the second term of the Expression (3), and the AC component which changes in the shape of a sine wave with the frequency fb as represented by the third term thereof. The AC signal will be referred to as "optical-beat signal". With the optical heterodyne interferometry, the amplitude of the optical-beat signal ($2a_s \cdot a_r$), the frequency ($f_b$), or the phase (Δ), is electrically measured, and the information is obtained based upon the amplitude (as) of the light signal, the frequency ($f_s$), or the phase ($\phi_s$).

Specifically, with the measurement of the dermal tissue, with the refractive indexes of the skin tissue which causes birefringence of the light as $n_x$ and $n_y$, and with the thickness of the tissue which the light passes through as d, the phase lags $\phi_x$ and $\phi_y$ are represented by the following Expressions (4) and (5).

$$\phi_x = \frac{2\pi n_x d}{\lambda} \quad (4)$$

$$\phi_y = \frac{2\pi n_y d}{\lambda} \quad (5)$$

With the present embodiment, the light having two frequency components slightly different one from another, such as STZL (Stabilized Transverse Zeeman Laser) oscillating light or the like, is cast onto the sample. In this case, the light intensity signal I detected by the photo-detector is represented as follows.

$$\begin{aligned} I &= \langle |E_x + E_y|^2 \rangle \quad (6) \\ &= \frac{a_x^2 + a_y^2}{2} + 2a_x a_y \cos(2\pi(f_x - f_y) \cdot t + (\phi_x - \phi_y)) \\ &= \frac{a_x^2 + a_y^2}{2} + 2a_x a_y \cos(2\pi f_b t + \Delta) \\ &= \frac{a_x^2 + a_y^2}{2} + 2a_x a_y \cos\left(2\pi f_b t + \frac{2\pi(n_x - n_y) \cdot d}{\lambda}\right) \\ &= \frac{a_x^2 + a_y^2}{2} + 2a_x a_y \cos\left(2\pi\left(f_b t + \frac{\delta n d}{\lambda}\right)\right) \end{aligned}$$

Note that reference character "Δ" represents the phase difference between the two components of the light, and reference character "δn" represents the difference in the refractive index (=magnitude of the birefringence). As can be understood from Expression (6), the phase difference between the two light components is represented by the phase difference of the beat signals. This enables measurement of the magnitude of the birefringence by measuring the phase of the optical-beat signals with the electronic phase meter 38 or the like.

Note that with the aforementioned measurement, there is the need to detect the direction of the principal axis beforehand, and to adjust the polarizing plane of the STZL oscillating light so as to precisely match the direction of the principal axis. Accordingly, there is the need to make measurement wherein the phase difference is detected while rotating the polarizing plane of the STZL oscillating light around the optical axis, thereby detecting the magnitude of the birefringence as well as the direction of the principal axis. However, such a measurement method leads to problems of an extremely complicated configuration of the authentication device, complicated user operations, and an excessively long detecting period of time. Furthermore, in this case, there is the need to stringently fix the position and the direction of the authentication device at the time of being fit by the user. Furthermore, the authentication device needs to be closely fit to the body of the user without looseness so as not to deviate from the fitting position even if the user moves.

With the present embodiment, the skin containing a fork structure of the subcutaneous blood vessel is used as the skin which is to be authenticated. The direction of the aforementioned principal axis can be easily obtained using the fork structure. For example, an arrangement may be made wherein the positional relation between the direction of the principal axis and the fork structure is determined and stored beforehand at the time of user registration, thereby enabling adjustment of the principal axis at the time of user authentication based upon the position and the direction of the blood-vessel fork structure in a simple manner.

On the other hand, an arrangement may be made wherein the deep-layer structure of the skin is detected using interference of the light, thereby solving the aforementioned problems, as well. That is to say, the object of the present invention is not to provide measurement of the magnitude of the birefringence, but it is an object thereof to provide a detecting method for detecting the unique properties of the user by measuring the internal structure of the skin through birefringence of the light or scattering thereof. With the present arrangement, the system causes interference between the incident light and the scattered light from the skin without any polarizer, and obtains the change in the frequency therebetween in the form of beat signals by detecting the interference of the light, using the fact that upon casting the light onto the skin, the frequency of the light changes due to back-scattering of the light or birefringence thereof occurring in the internal structure of the skin such as the dermal layer or the like.

Figure 5:
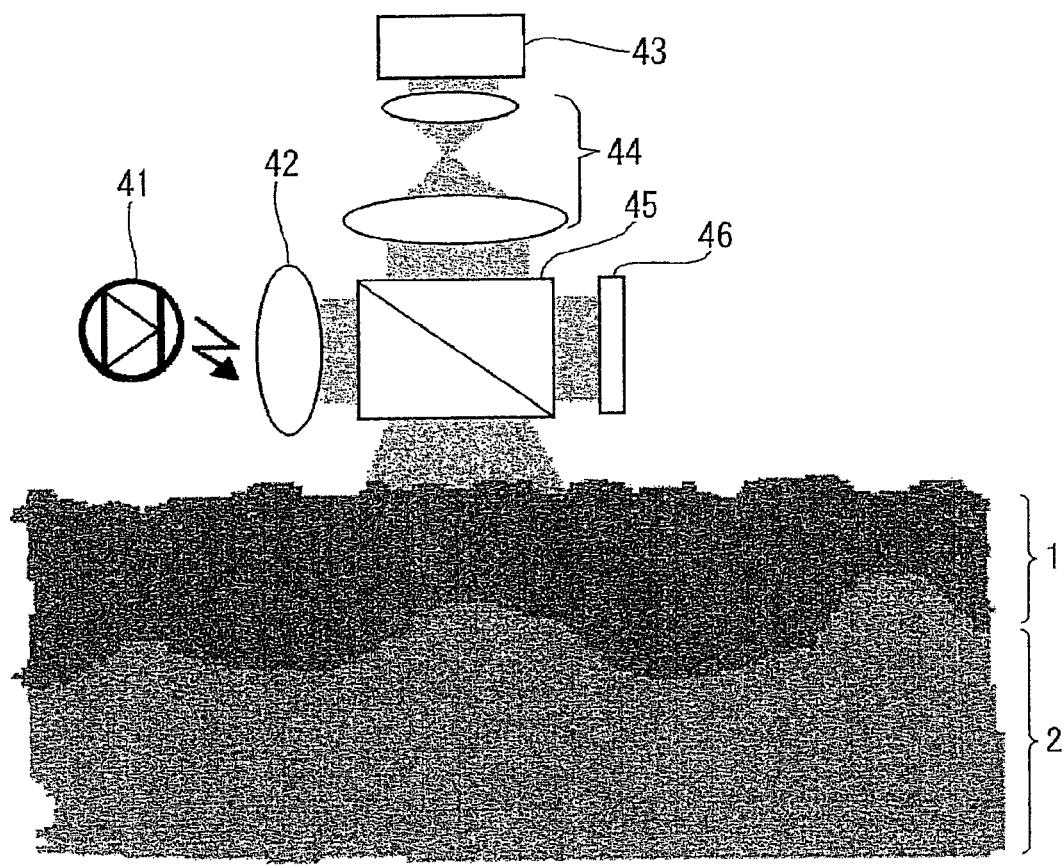
FIG. 5 is a schematic diagram which shows an example of a detecting device (authentication device) for detecting the tissue pattern beneath epidermis using the scattering property pattern obtained due to interference of the light returning from the skin.

FIG. 5 shows a configuration example of such a detecting device. The detecting device has the same configuration as with the detecting device shown in FIG. 2 wherein an illumination optical system formed of an illumination light source 41 and an optical lens 42, and an imaging optical system formed of an imaging device 43 such as a CCD or the like and an imaging lens 44, are disposed orthogonal one to another through a half mirror 45. Note that with the present arrangement, neither of the illumination optical system and the imaging optical system include a polarizing plate. Instead of the polarizing plates, the present detecting device includes a reference mirror 46 for introducing a part of the illumination light cast from the light source 41 of the illumination optical system to the imaging device 43 of the imaging optical system.

A part of the light emitted from the light source 41 such as a white LED or the like is cast on the surface of the skin through the half mirror 45. Upon casting the aforementioned part of the illumination light onto the skin, various kinds of scattering of the light and birefringence thereof occur in the internal structure of the skin, and the scattered light returns to the half mirror 45. The system causes a beat phenomenon (interference) between the returning light and the light which is reflected from the half mirror 45 onto the reference mirror 46, and is reflected by the reference mirror 46, at the same time of illumination, whereby an interference pattern is formed on the imaging device 43.

Figure 6:
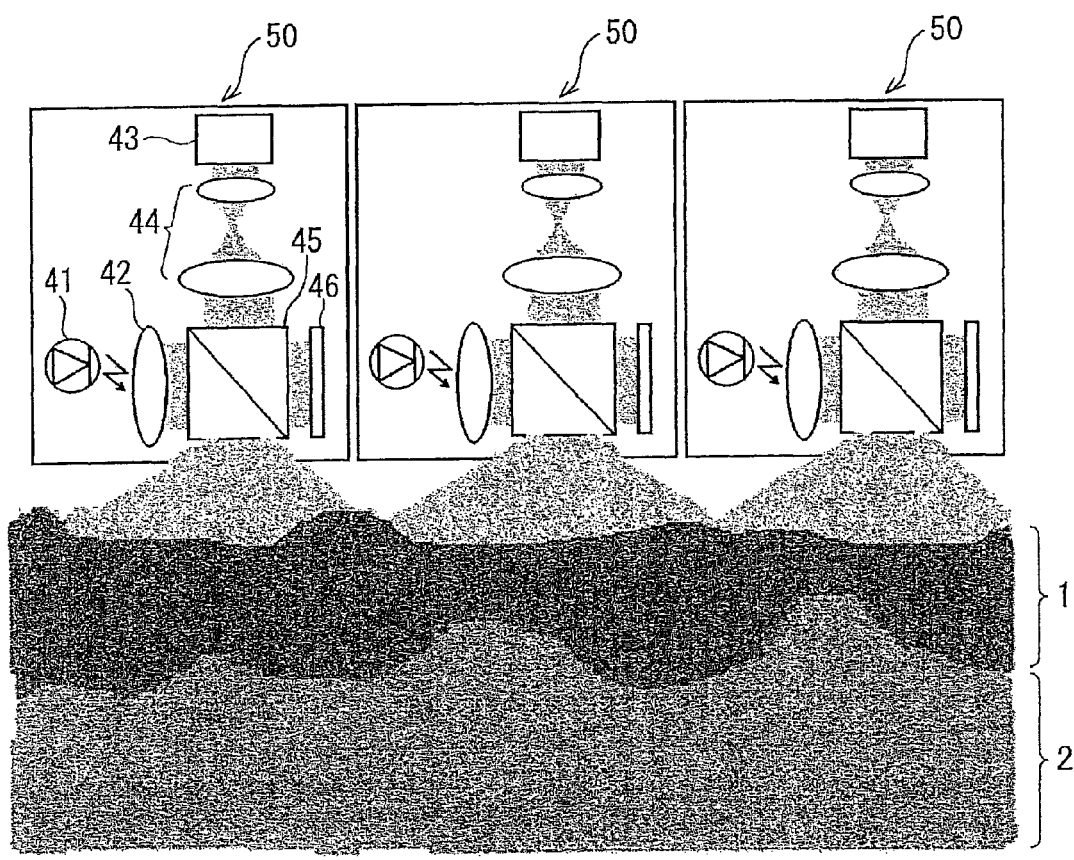
FIG. 6 is a schematic diagram which shows an example of a detecting device (authentication device) having a configuration wherein multiple beat detecting devices are arrayed.
Figure 7:
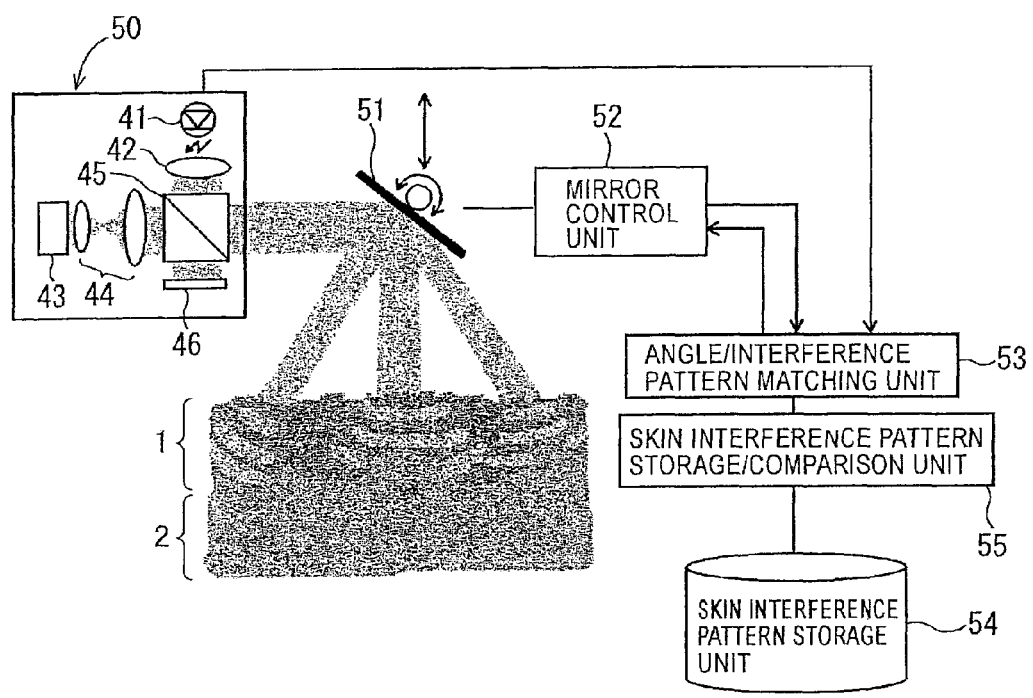
FIG. 7 is a schematic diagram which shows an example of a detecting device (authentication device) having a configuration wherein a moving mirror is provided to an illumination unit for casting light onto the skin.

Furthermore, an arrangement may be made wherein the aforementioned beat is detected for each region in a detecting range for the skin, thereby obtaining a continuous pattern of the internal structure beneath the epidermis based upon the beat pattern thus obtained. Specific arrangement examples for obtaining the aforementioned continuous pattern include: an arrangement wherein multiple beat detecting devices are arrayed as shown in FIG. 6; and an arrangement wherein the illumination unit includes a moving mirror for casting the light onto each region of the skin as shown in FIG. 7. The former arrangement has a configuration wherein the multiple beat detecting devices 50 are arrayed in the shape of a so-called "array", each of which comprise the illumination optical system formed of the aforementioned illumination light source 41 and the optical lens 42, and the imaging optical system formed of the imaging device 43 such as a CCD or the like and the optical lens 44, disposed orthogonal one to another through the half mirror 45, thereby obtaining a continuous pattern of the internal structure beneath the epidermis based upon the signals detected with each beat detecting device 50.

On the other hand, with the latter arrangement, illumination of the light and detection of the returning light with each beat detecting device 50, are performed using the aforementioned moving mirror 51. The latter arrangement has a configuration wherein a mirror control unit 52 controls the angle of the moving mirror 51 according to control information from an angle/interference-pattern adjusting unit 53. The aforementioned angle/interference-pattern adjusting unit 53 receives interference-pattern information from the aforementioned beat detecting device 50. Then, the received interference pattern is compared to an interference pattern which has been stored and registered beforehand in a skin-interference pattern storage unit 54, in a skin-interference pattern storage/comparison unit 55, thereby enabling biometric authentication.

The aforementioned methods do not require a polarizer which is indispensable for detection of the phase difference or the like, thereby having the advantage of enabling authentication without precise adjustment of the optical axis. This allows stable authentication even if the direction of a wristwatch-type authentication device or the like, fit by the user, changes due to failure in being fit by the user, looseness at the time of being fit by the user, or the like, for example.

In practical situations, there is the need to adjust the authentication device so as to face the tissue which is to be authenticated in a case wherein the authentication device is fit by the user with some looseness, or the like. On the other hand, an arrangement may be made wherein the interference pattern is registered for a wide skin region including the target region. However, such an arrangement requires pattern matching processing for searching the aforementioned wide region for a matched pattern, leading to a great processing load. Such a great load is undesirable for a mobile authentication device from the perspective of power consumption and so forth.

For example, let us consider a special case of the biometric authentication using the skin pattern, such as fingerprints or the like. In this case, the center of a whirl-shaped pattern, a horseshoe-shaped pattern, or the like, can be easily detected, and furthermore, the area of the surface of the finger having such a structure is narrow, thereby facilitating search for the position which is to be authenticated. However, other ordinary portions have relatively large area as compared with the fingertip, and have fine skin pattern having no geometric structure which facilitates search for the position which is to be authenticated, unlike the whirl-shaped pattern of the fingerprints, except for limited special portions, leading to extreme difficulty in search for the region which is to be authenticated.

In order to solve the aforementioned problem, an arrangement may be made wherein the skin pattern is registered for a wide region beforehand as described above, and the system determines whether or not the pattern detected at the time of authentication is included in the aforementioned registered pattern. However, such an arrangement leads to registration for an excessively large area, which is troublesome, and leads to a problem of excessive processing load and excessive processing period of time of the authentication device at the time of authentication. With an ideal arrangement, the skin pattern is preferably registered for the whole body. However, such an arrangement is not undesirable from the practical perspective as described above. Furthermore, in this case, it is difficult to determine the "wide region". In practical situations, the authentication device may deviate from the region at the time of authentication due to flexibility of the human body, or difference in the position to which the authentication device is fit for each authentication.

Description will be made below regarding an effective method for searching for the target region of the skin which is to be authenticated. With the present method, the near-infrared light is employed as the incident light instead of white light, which has a wavelength range which allows the light to pass through the tissue with high transmissivity, and causes exceptional absorption of the light by reduced hemoglobin contained in venous blood or the like. The authentication device detects a vein pattern using the detected back-scattered light from the subcutaneous tissue, and searches for the target region which is to be authenticated based upon the vein pattern thus obtained. With the present arrangement, the target region which is to be authenticated is a region containing a distinctive pattern or a vein fork structure. This allows stable search for the same skin region which is to be authentication in a sure manner, even if a wristwatch-type person authentication device is fit by the user with some displacement or looseness on a contact face between the authentication device and the skin of the user.

Figure 8:
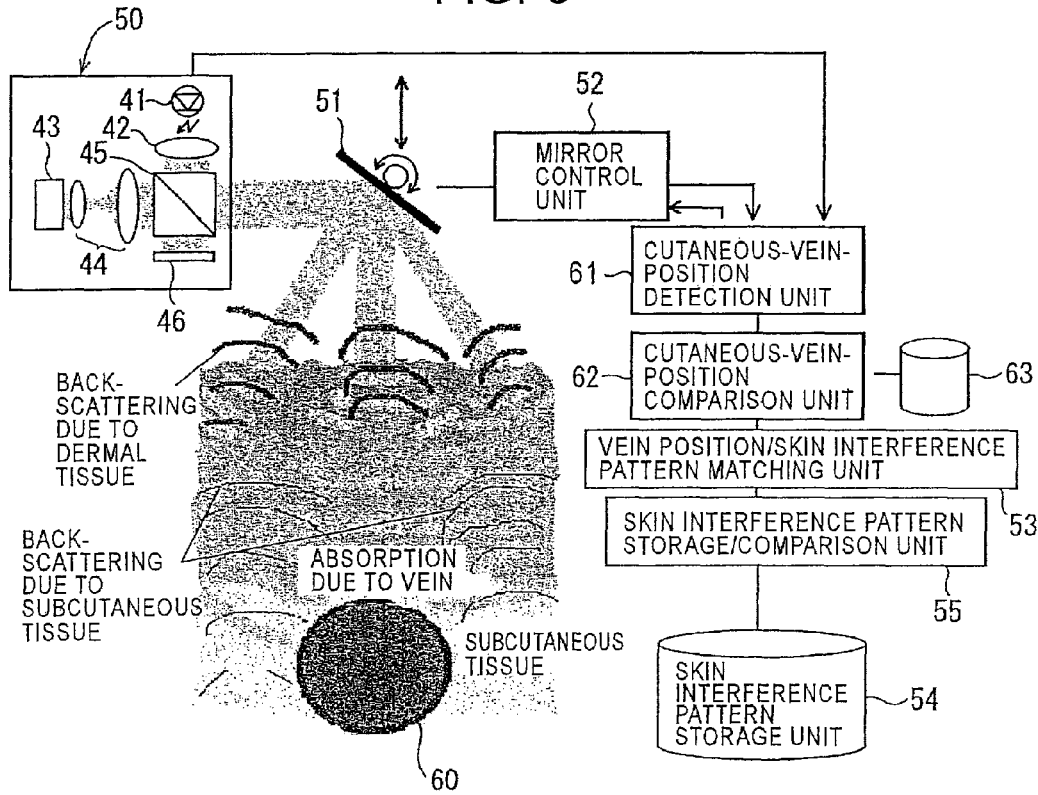
FIG. 8 is a schematic diagram which shows an example of a detecting device (authentication device) having a function for determining a portion which is to be authenticated, based upon a vein pattern.

FIG. 8 shows an example of a detecting device having a function for searching for the target region which is to be authenticated based upon the vein pattern. The detecting device shown in FIG. 8 has the same configuration as in FIG. 7, except for a configuration wherein a near-infrared light source is employed as the light source 41 for the beat detecting device 50, and a subcutaneous vein position detecting unit 61, a subcutaneous vein position comparison unit 62, and a vein data storage unit 63 for storing vein data, are further included. Such a configuration allows acquisition of an image of blood capillaries of a subcutaneous vein 60 extending along the dermal layer, which is a vein positioned at the shallowest portion of the skin.

Figure 9:
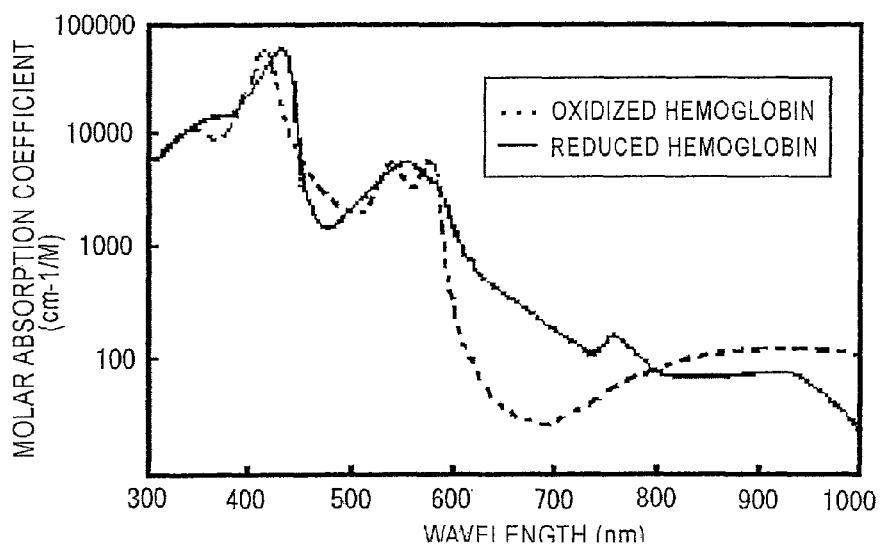
FIG. 9 is a property chart which shows absorption spectra of oxidized hemoglobin and reduced hemoglobin.
Figure 10:
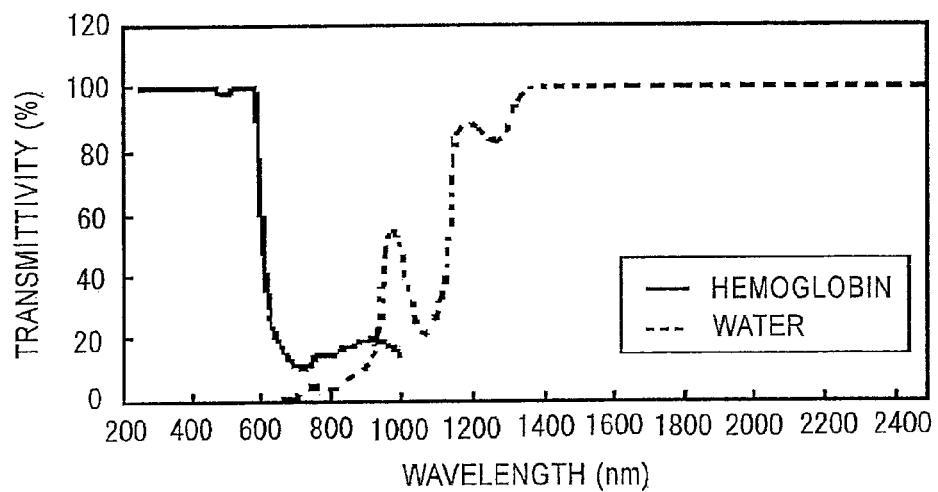
FIG. 10 is a property chart which shows difference in transmissivity between hemoglobin and water in living tissue.

The tissue exhibits marked low absorbance for the infrared light in a wavelength range of 700 to 1200 nm, i.e., the tissue has properties which allow the light to readily pass therethrough, and accordingly, the wavelength range is referred to as "the window of spectroscopic analysis". Note that while the epidermal tissue has the properties which cause reflection and scattering of visible light and ultraviolet light, nearly approximately 80% of the light in the aforementioned wavelength range passes through the tissue. On the other hand, of the near-infrared light in such a wavelength range having such properties, the near-infrared light at a particular wavelength is selectively absorbed by hemoglobin contained in blood. Specifically, as shown in FIG. 9, the oxidized hemoglobin ($HbO_2$) exhibits the same absorbance as with the reduced hemoglobin (Hb) at a wavelength of 805 nm. On the other hand, the reduced hemoglobin (Hb) exhibits higher absorbance than with the oxidized hemoglobin ($HbO_2$) at a wavelength of 660 nm, and the oxidized hemoglobin (HbO$_2$) exhibits higher absorbance than with the reduced hemoglobin (Hb) at a wavelength of 940 nm. Furthermore, the hemoglobin has different spectroscopic properties from those of water in the tissue, as shown in FIG. 10.

Accordingly, a blood-vessel image can be obtained by detecting difference between hemoglobin and water within the tissue using the aforementioned properties. Furthermore, difference between an artery and a vein can be detected using difference in absorbance therebetween at a suitably-selected wavelength. In order to detect a vein pattern, an arrangement may be made wherein the light source includes illumination means for illuminating near-infrared light with a wavelength of 805 nm, and the near-infrared light is cast onto the tissue through a polarizing plate, for example. The incident light causes three kinds of phenomena of reflection of the light, scattering thereof, and birefringence thereof, and the returning light due to the aforementioned kinds of phenomena is detected. In this case, the reflected light from the surface of the skin deteriorates the quality of the image of the internal structure beneath the skin surface. Accordingly, with the present arrangement, an image of the internal structure is taken with a CCD camera or the like through the polarizing plate 26 disposed with the polarizing plane orthogonal to that of the polarizing plate 23. This allows image taking using only depolarized light such as scattered light and light split due to birefringence while filtering the reflected light with the same polarizing plane as with the incident light, which has been reflected by the horny layer, the lucid layer, the granular layer, and so forth, forming the epidermal tissue.

While description has been made regarding the detecting devices shown in FIG. 2 and FIG. 3, wherein the dermal layer is detected by eliminating the returning light other than the scattered light from the tissue which is to be detected, with the present arrangement, the incident light with a suitably-selected wavelength is selectively absorbed in blood capillaries within the dermal layer since the materials in blood vessels within skin tissue other than hemoglobin exhibit low absorbance, i.e., have high transmissivity at the wavelength, unlike a case of using the white light source, thereby obtaining a clear image of a blood-capillary pattern within the dermal layer with back-scattering of the light at a deeper portion as a background.

The pattern formed of blood flow in the blood capillaries is unique to individual tissue. Furthermore, in the event that the tissue is cut off from the body of the user, the aforementioned pattern is immediately lost due to contraction of blood vessels, retention of blood, lost of blood, and so forth. Furthermore, an arrangement may be made wherein the system detects change in absorbance corresponding to the heart beat using the absorbance of oxidized hemoglobin at a wavelength of 940 nm, thereby enabling living-tissue discrimination, as well as acquisition of an image of the pattern of the subcutaneous blood capillaries. Furthermore, the present arrangement may include an additional method wherein determination is made whether the tissue belongs to normal live tissue or dead tissue cut off from the user by detecting reduction or loss of the absorbance of oxidized hemoglobin at a wavelength of 940 nm due to extreme reduction of oxygen concentration within the tissue due to failure in pulmonary circulation, using the fact that different types of hemoglobin exhibit different absorbance, e.g., the fact that the deoxidized hemoglobin exhibits higher absorbance than with the oxidized hemoglobin at a wavelength of 660 nm, the fact that the oxidized hemoglobin exhibits higher absorbance than with the deoxidized hemoglobin at a wavelength of 940 nm, and so forth.

The aforementioned methods integrate the biometric authentication and the living-tissue discrimination. That is to say, the system can discriminate and reject the tissue cut off from the body of the user by detecting absence of blood flow even if the tissue is alive by soaking in a physiological salt solution. In this case, the tissue which is to be authenticated needs to exhibit normal pulmonary circulation, normal heart beat, normal blood flow, and normal hemoglobin ratio in blood. Accordingly, if other persons cut off the arm of the user with a surgical method for "spoofing", there is the need to connect the blood vessels of the arm to a heart-lung machine, and to precisely reproduce the heat-beat wave. Accordingly, it would be difficult to make "spoofing" in the present situation wherein mobile heart-lung machines are unavailable. Even if mobile heart-lung machines become available in the future, such "spoofing" would require advanced surgical techniques and surgical equipment for performing: cutting off of the arm from the body; connection of the blood vessels of the arm to a heart-lung machine; treatment for fine blood vessels and nerves; prevention of change in the tissue due to vital reaction caused due to cutting off of the arm; stabilization of the tissue after resumption of blood flow; and so forth, which is far from being realistic. On the other hand, it is even more difficult to create a forgery of the tissue having precisely the same three-dimensional structure of fine blood capillaries which causes the same scattering of the light, instead of the tissue cut of from the body of the user.

Next, description will be made regarding a detecting method for detecting a pattern beneath the epidermis using the differential interference method. The differential interference method is one of observation methods using a microscope, wherein the phase difference between the illumination light and the returning light, which is dependent upon the thickness of the sample and the difference in the refractive indexes, is converted into contrast or contrast in color, thereby enabling observation which provides impression of solidity. In general, it is difficult to detect the dermal layer through a bright field optical system or visual observation. The present arrangement has been made using the fact that a differential interference optical system allows the user to observe even cell nuclei wherein observation is difficult using an ordinary microscope without staining. Note that while the aforementioned differential interference optical system allows detection of the dermal layer in a case wherein the dermal layer appears as a top layer, it is difficult to detect the dermal layer in normal situations. That is to say, in normal situation wherein the dermal layer is covered with the epidermal layer, while the surface of the epidermal layer can be observed with such a method, detection of the epidermal layer is difficult due to reflection of light, scattering thereof, and shielding thereof, without some particular method.

While a white light source is employed for an ordinary differential interference optical system, with the present invention, a near-infrared light source and a near-infrared CCD are employed as well as a differential interference optical system, using the fact that the epidermal layer exhibits high transmissivity in a wavelength length of red light to near-infrared light. This enables detection of the roughness pattern of the dermal layer beneath the epidermis in a noninvasive manner.

Figure 11:
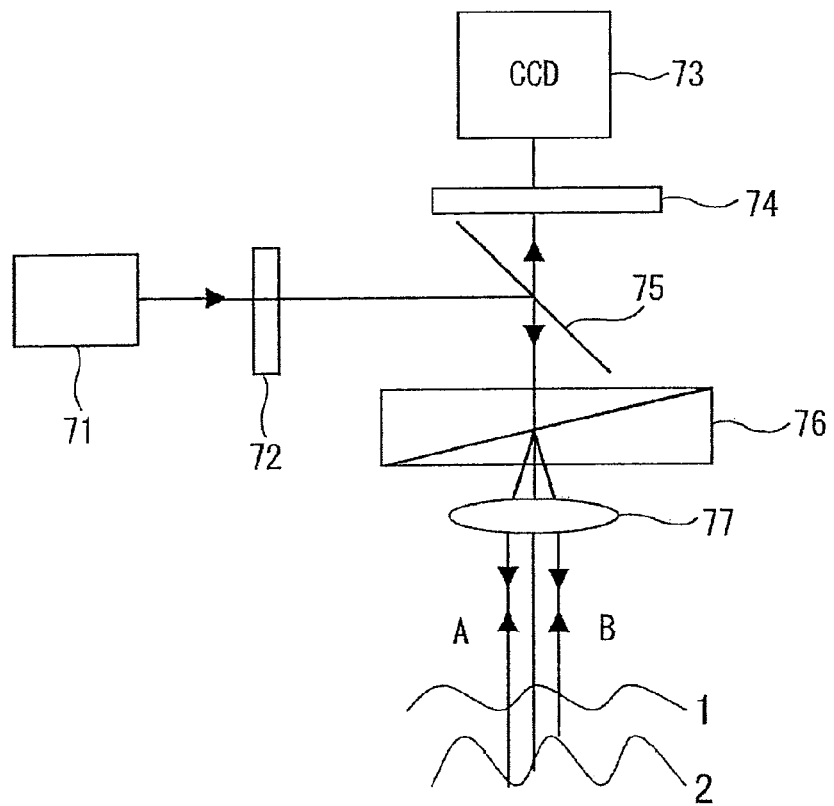
FIG. 11 is a schematic diagram which shows an example of a detecting device (authentication device) for performing pattern detection with the differential interference method using near-infrared light.

FIG. 11 shows a specific arrangement example. A detecting device comprises an illumination optical system including a near-infrared light source 71, a polarizing prism 72, and an imaging optical system including an imaging device 73 such as a CCD or the like, and a polarizing prism 74. The illumination optical system and the imaging optical system are disposed with the optical paths orthogonal one to another through a half mirror 75. The illumination light is cast onto the skin from the illumination optical system through reflection by the half mirror 75, and the returning light (reflected light) passes through the half mirror 75, whereby the light reaches the imaging optical system. Note that a Wollaston prism 76 and an objective lens 77 are disposed on the optical path between the aforementioned half mirror 75 and the skin.

The illumination light cast from the near-infrared light source 71 is converted into light with the same polarizing plane by the polarizing prism 72, and is reflected by the half mirror 75 toward the Wollaston prism 76. The illumination light cast onto the Wollaston prism 76 is split into two beams (beam A and beam B) with the polarizing planes orthogonal one to another, following which the two beams are cast onto the object (tissue). Note that the distance between the beam A and the beam B is equal to or less than the resolution of the objective lens. Subsequently, the two beams reflected by the object are recombined into a single beam by the Wollaston prism 76. The single beam thus recombined passes through the half mirror 75, and is converted into the light with the same polarizing plane by the polarizing prism 74. With such a configuration, reflection of the two beams A and B at a stepped portion leads to optical-path difference therebetween, leading to interference thereof at the time of the beam passing through the polarizing prism 74. Note that in a case wherein the optical-path difference matches half the wavelength of the beams A and B, the light appears brightest due to interference. The interference pattern can be observed with an ordinary differential interference optical system employing a white light source, thereby enabling the user to make visual observation of a transparent object with impression of solidity. However, with the present arrangement using near-infrared light, visual observation is difficult. Accordingly, the present arrangement includes the imaging device 73 such as a CCD for taking a near-infrared image.

[Method Using the Electric Properties]

Next, description will be made regarding another method according to the present invention, wherein the roughness pattern or the like of the deep-layer structure (e.g., the dermal tissue) beneath the epidermis using the difference in the electric properties, whereby biometric authentication is performed.

Figure 12:
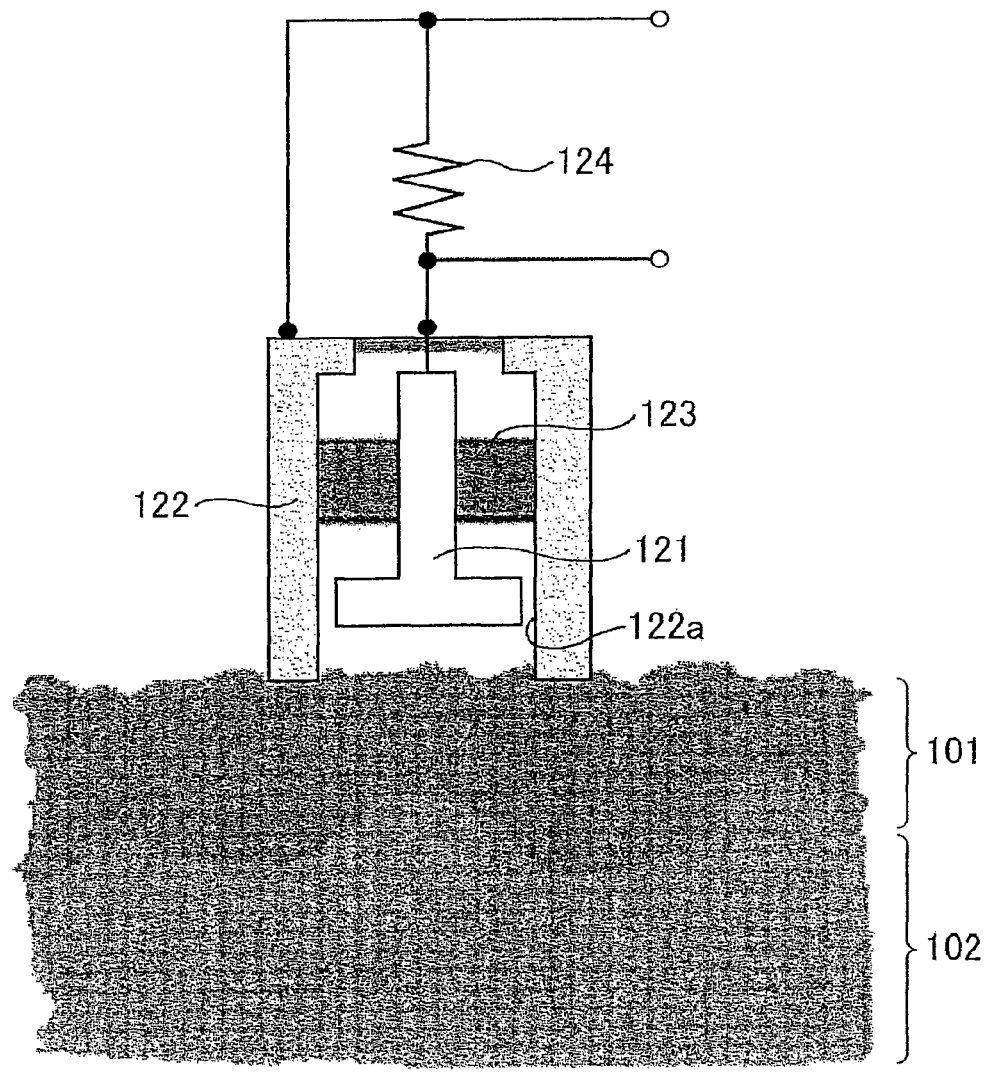
FIG. 12 is a schematic diagram which shows an example of a skin-surface electric-potential detecting device.

FIG. 12 shows an arrangement example of a detecting device wherein the electric potential of the skin is detected using electrostatic induction, and the depth at which the dermal tissue is positioned is detected based upon the detected electric potential, whereby the internal pattern beneath the epidermis is obtained. With the present detecting device, the electrostatic capacitance between the detecting electrode and the dermal layer is detected using the fact that the epidermal layer relatively exhibits a nature near being dielectric while the dermal layer exhibits high electric conductivity.

In order to detect the electrostatic capacitance, the detecting device shown in FIG. 12 includes multiple fine electrodes 121 two-dimensionally arrayed with micromachining technology so as to form a detecting electrode plane for being in contact with the surface of the skin. At the time of measurement, electrostatic capacitance is formed between each fine electrode 121 on the detecting electrode plane and the dermal layer. Then, the distance distribution regarding the subcutaneous electric-conductive layer underneath each fine electrode 121 is calculated based upon the electrostatic capacitance which is dependent upon the distance between the electrode and the electric-conductive layer, thereby obtaining the subcutaneous tissue structure. That is to say, with the present detecting device, electrostatic capacitance is formed between: each of the fine electrodes 121 forming the detecting electrode plane positioned parallel to the skin; and the skin, and the terminal voltage of each electric capacitance is measured, whereby the dermal-layer structure is obtained.

A cylindrical metal casing 22 stores the aforementioned fine electrode 121 held by an insulating support member 123. The fine electrode 121 is electrically connected to the casing 22 through a resistor 24 having high electrical resistance. There is a gap between the fine electrode 121 and the casing 122. At the time of the casing 122 being in contact with the skin, the aforementioned fine electrode 121 faces the skin with a predetermined gap therebetween at an opening 122a of the casing 122.

Note that the present detecting device has a problem of extremely unstable output signals since the surface of the skin having the nature near a dielectric is readily affected by electrostatic induction due to noise or the like from an external AC power supply or a fluorescent lamp, and the surface structure of the skin readily exhibits various conditions due to separation of the horny layer, or the like. In order to solve the aforementioned problem, a method is known for detecting fingerprints or the like, wherein output signals are detected while applying high-frequency electric signals to the human body. Such a method may be applied to detection of the tissue structure wherein the epidermal pattern corresponds to the dermal pattern, such as the fingerprints or the like. However, the aforementioned method cannot be applied to detection of the dermal pattern of other skin tissue wherein the epidermal pattern does not correspond to the dermal pattern. The reason is that in this case, the detecting device detects the epidermal pattern. The epidermal pattern which does not correspond to the dermal pattern does not exhibit sufficient stability, unlike the fingerprints, and accordingly, the aforementioned method cannot be employed for the biometric authentication using detection of such tissue.

Figure 13:
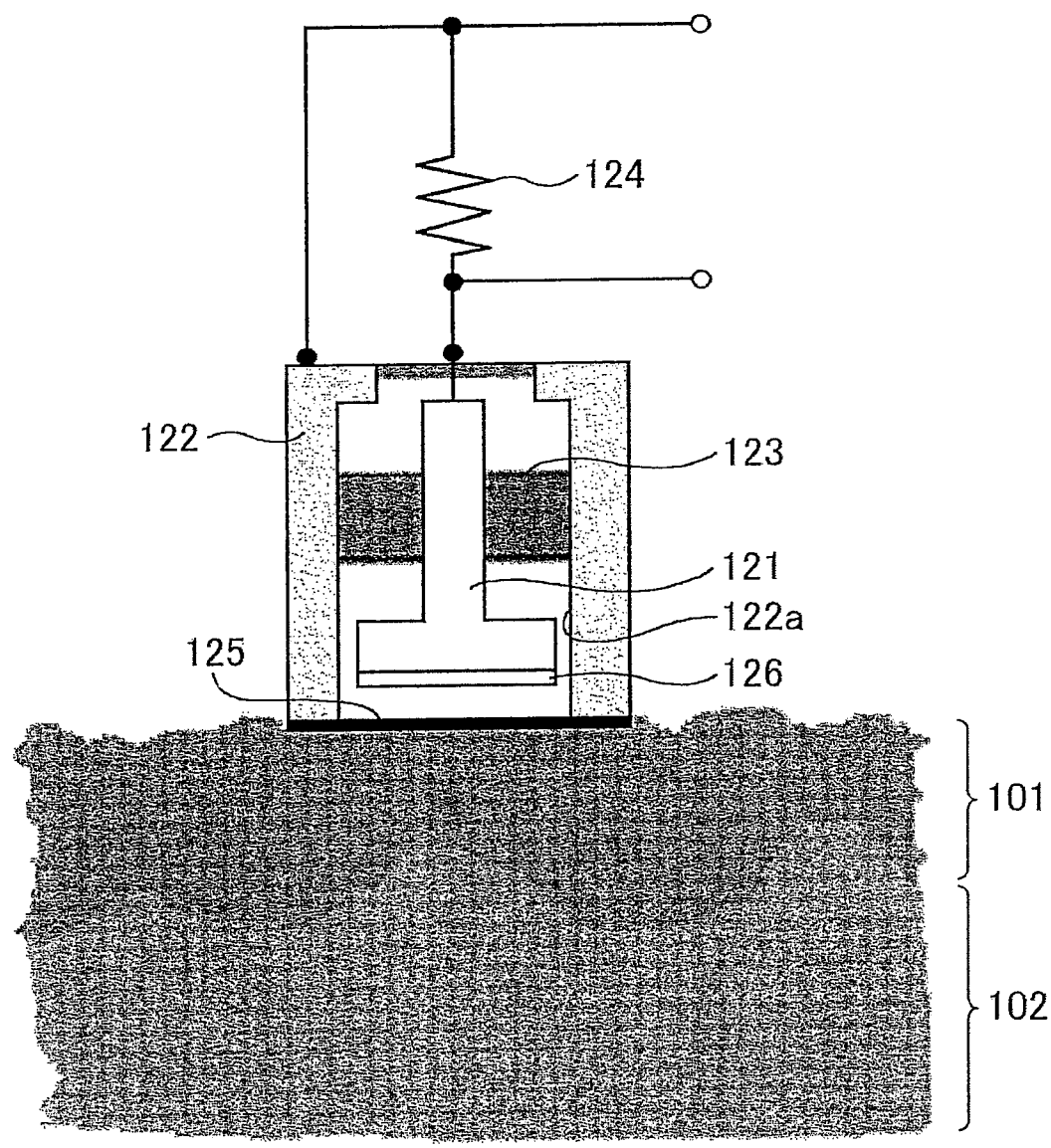
FIG. 13 is another schematic diagram which shows an example of a skin-surface electric-potential detecting device.

Accordingly, in order to solve the aforementioned problems, the detecting device according to the present arrangement includes a dielectric thin film 125 disposed at the opening of the metal casing 122 as shown in FIG. 13, for example. At the time of measurement, the dielectric thin film 125 is positioned between the metal casing 122 and the skin with which the detecting device is pressed into contact. At the same time, the dielectric thin film 125 is in contact with the metal casing 122 which stores the fine electrode 121 and is connected to the ground, whereby electrostatic capacitance is formed between casing 122 and the skin, as well. Furthermore, such a configuration has the advantage of suppressing adverse effects due to unstable conditions of the surface structure of the horny tissue of the skin.

Furthermore, the detecting device includes an electret film 126 on the surface of each fine electrode 121 forming the detecting electrode plane. The electret film 126 is formed of a tetrafluoroethylene film or the like and semi-permanently holds electric charges. With the present arrangement, the electrostatic capacitance is formed between the fine electrode 121 and the dermal tissue (electrically conductive tissue) with a bias voltage due to the permanent polarization of the electret film 126 without externally applying high frequency bias voltage, thereby enabling detection of the distribution of difference in the electrostatic capacitance between the fine electrodes 121, and thereby enabling detection of the deep-layer structure of the skin such as the dermal layer or the like covered with the epidermal tissue of the skin in a noninvasive manner.

With the detecting device having a configuration shown in FIG. 13, the fine electrode 121 having the electret film 126 is disposed at the opening 122a of the aforementioned casing 122. At the time of measurement, the detecting device is positioned such that the opening 122a faces the tissue, whereby electrostatic capacitance is formed between the fine electrode 121 and the skin through the dielectric thin film 125. On the other hand, the casing 122 serves as a counter electrode as to the skin, and is grounded. On the other hand, the electrode within the opening 122a serves as a detection electrode. Accordingly, change in the electric potential due to the epidermal tissue is common to both the electrodes, and accordingly, the components thereof exhibit reverse polarity between both the electrodes, leading to canceling out one another.

On the other hand, change in the electric potential at a deep portion of the skin causes electrostatic capacitance between the dermal layer having electric conductivity and the fine electrode 121 serving as a detection electrode, thereby enabling detection of change in the electric potential at the deep portion of the skin. On the other hand, no bias voltage due to an electret film or the like is applied to the capacitance formed by the casing 122, and accordingly, change in the electric potential of the deep layer of the skin is not detected by measuring the capacitance formed by the casing 122 due to charges on the surface of the skin. Thus, the present arrangement allows the detecting device to precisely detect changes in the electric potential of the deep layer of the skin alone, while canceling out adverse effects due to electrostatic induction of the skin surface, charges thereon, or the like.

Figure 14:
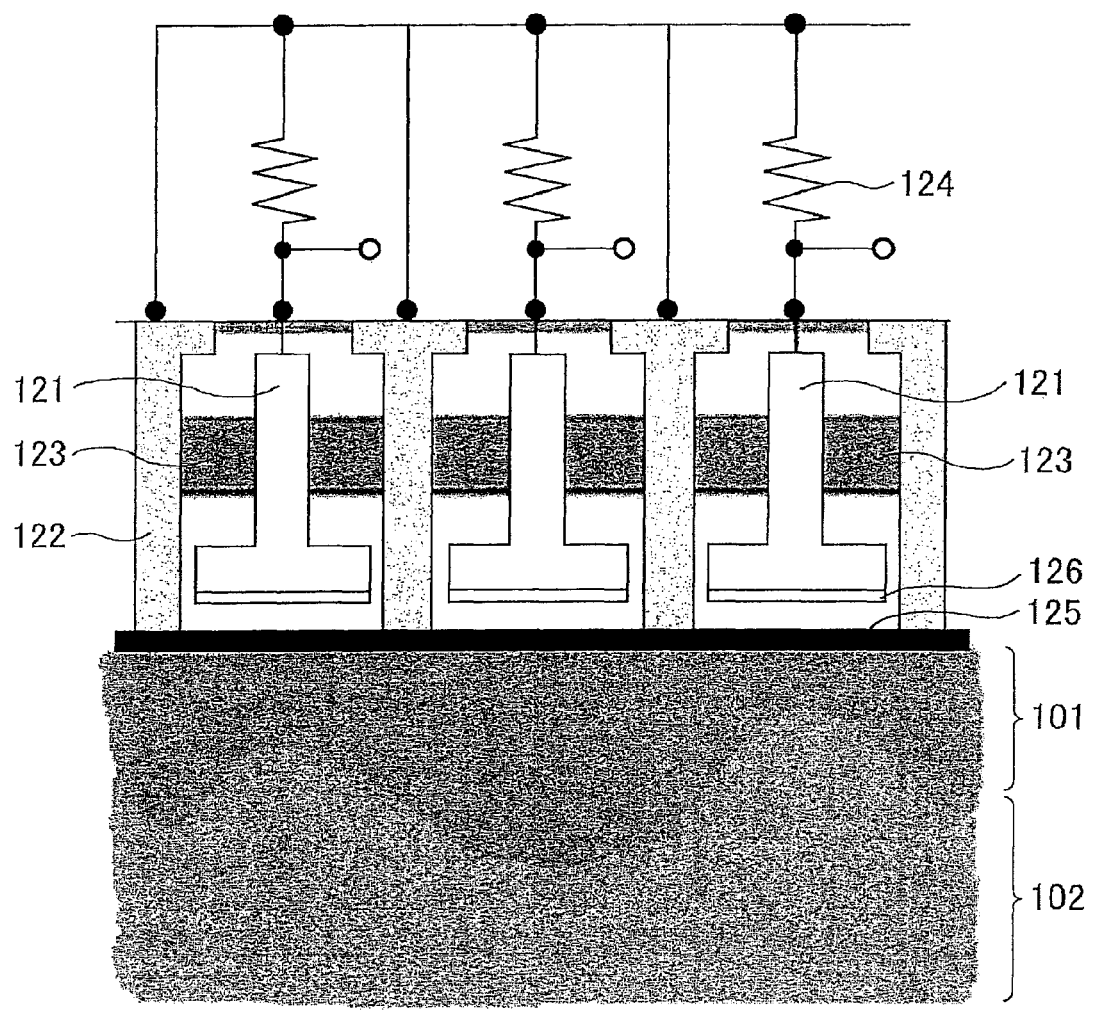
FIG. 14 is a schematic diagram which shows a subcutaneous-tissue pattern detecting device having a configuration wherein the multiple skin-surface electric-potential detecting devices are two-dimensionally arrayed.

With an arrangement wherein the change in the electric potential is measured by extracting from change in the electrostatic capacitance at each point on the tissue, different amplitude is detected for each point due to variation in the electrostatic capacitance dependent upon the thickness of the epidermis. FIG. 14 shows an arrangement having a configuration wherein the aforementioned detection electrodes (fine electrodes 121) are two-dimensionally arrayed in the form of a matrix, and having a function wherein the conductive-layer structure beneath the epidermis is obtained using the amplitude of the electric potential which is changed synchronously with the entire human body due to walking or the like.

Figure 15:
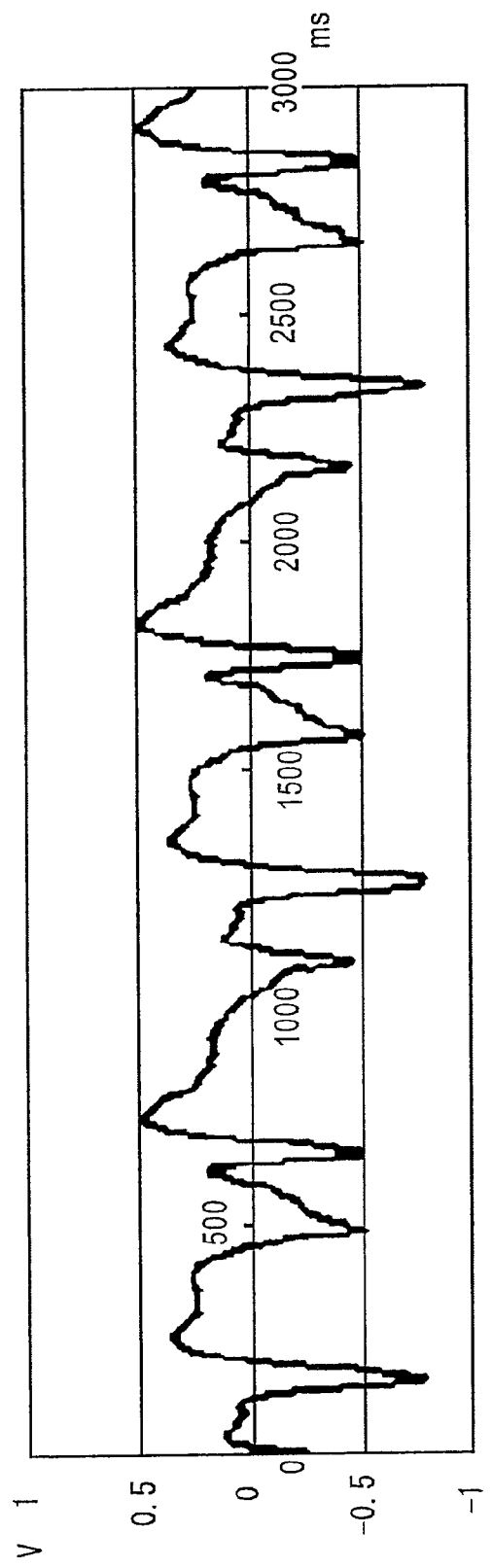
FIG. 15 is a waveform chart which shows an example of an electric-potential waveform observed when walking.

As shown in FIG. 15, at the time of walking, change in the electric charge occurs with a single phase, synchronously with the entire human body due to grounding and electrical floating between the foot and the floor. Description will be made below regarding change in charge on the human body due to walking. That is to say, the waveform which is formed on the skin due to walking and is detected by an electrostatic-capacitance sensor, is formed according to two mechanisms as follows.

The first mechanism is essentially the same as with a capacitor microphone. The capacitor microphone has a mechanism wherein the gap between a diaphragm and an electret electrode changes due to vibration of the diaphragm, the electrostatic capacitance (C) of the gap changes due to the vibration, and the signals due to change in the electrostatic capacitance are subjected to impedance conversion through the gate of an FET, whereby the vibration of the diaphragm is detected. The detecting device according to the present invention has the same configuration as with the capacitance microphone, except for the configuration wherein a dielectric film is included instead of the diaphragm, which is pressed into contact with the tissue of the human body at the time of measurement, whereby charge coupling occurs between the detecting device and the tissue of the human body through the dielectric film. At the same time, capacitance (electrostatic capacitance) is formed by the gap between the electret electrode and the dielectric film, and furthermore, the electrostatic capacitance of the human body and the electrostatic capacitance of the gap are combined due to charge coupling.

In this state, change in the electrostatic capacitance due to interaction between the human body and the external environment (e.g., grounded object), e.g., walking or the like, is directly detected by the detecting device in the form of waveform signals, like the capacitance microphone.

Here, the electrostatic capacitance (C) of the human body changes corresponding to the distance between the ground and the position of the foot in the space. That is to say, in a case wherein the foot is in contact with the ground, the capacitance of the human body is great. On the other hand, in a case wherein the foot is positioned away from the ground, the electrostatic capacitance of the human body is extremely small due to an air layer having a low dielectric constant between the sole (of a shoe) and the ground. On the other hand, the greater the contact area between the foot and the ground, the grater the electrostatic capacitance is. Note that the electrostatic capacitance C is represented by the following Expression.

$C = \in \cdot S/d$ [F] ($\in$ represents dielectric constant of a medium with which the gap between the electrodes is filled, $S$ represents the area of the electrode, and d represents the distance between the electrodes)

As can be understood from the above Expression, the greater the contact area between the foot and the ground is, i.e., the greater the area of the electrode (S) is, the greater the electrostatic capacitance is.

The second mechanism is that the electrode itself makes an action serving as a charge sensor. That is to say, the electrode stored in the metal casing of the detecting device, which faces the tissue through the dielectric film, detects change in the electric potential induced on the dielectric film due to charge of the human body in the form of a waveform.

It is assumed that the waveform detected on the human body is formed according to the two mechanisms as described above, i.e., it is assumed that the waveform is essentially formed not due to the electric potential, but due to charge. That is to say, it is assumed that the phenomenon represented by the following Expression occurs. Note that the assumption has been confirmed by reproducing the observed waveform by simulation using the equivalent circuit method.

$Q$ (charge)=$C$ (electrostatic capacitance)~$V$ (voltage of the electrode)

While change in the aforementioned charge exhibits generally the same waveform over the entire human body, the waveform exhibits different amplitude corresponding to the fine structure of the skin tissue, in particular, corresponding to the relation between the epidermis and the dermal layer. The waveform due to change in charge changes synchronously over the entire human body. Accordingly, with the present arrangement, comparison is made for the amplitude of the waveform detected by each of the fine detecting electrodes arrayed in the form of a two-dimensional matrix, thereby measuring the distance between the electrode and the dermal layer for each electrode, and thereby obtaining the structure beneath the epidermis.

As described above, with the present arrangement, change in charge occurring due to walking or other motions is detected with each fine electrode 121 without active charge generating means such as an electrode for applying charges or the like, using the fact that charge changes on the human body due to interaction between the foot and the ground by motions wherein the foot is off the ground and touches the ground at the time of walking or the like. Then, the difference in the amplitude between the waveforms occurring due to change in charge synchronously over the entire human body due to motions of the user is converted into the distance between the surface of the skin and the tissue beneath the epidermis, thereby detecting the deep-layer structure beneath the epidermis such as the dermal layer or the like underneath the detecting electrode.

In general, it is assumed that conventional electrostatic-capacitance methods have been applied to a stationary authentication device which is grounded. Accordingly, at the time of a wearable authentication device employing such a conventional method being fit by the user for performing authentication of the user, in a case wherein the user walks on a carpet in a low humidity environment in winter, both the detecting electrode and the grounded portion may be greatly charged, leading to difficulty in precise detection. The reason is that with the wearable authentication device, the grounded portion is positioned on the human body.

In order to solve the aforementioned problems, a method or the like has been proposed, wherein additional transmission means such as an electrode, a transducer, or the like, is provided for being in contact with the human body in addition to the detecting electrodes, a predetermined ultrasonic waves or high-frequency signals are actively applied with the transmission means so as to propagate on the human body, the signals thus propagating on the human body are detected with fine electrodes on the skin, and determination is made whether or not the face of each fine electrode is in contact with the skin, thereby obtaining the fingerprint pattern of the user. However, such a method leads to a complicated configuration, as well as leading to a problem that the tissue which is to be authenticated is restricted to a special portion such as fingerprints, a part of the skin of the palm, and so forth. For example, let us consider an authentication method wherein the authentication is performed using the skin underneath a ring including a built-in authentication device. In this case, the pattern of the epidermal layer at such a portion, such as wrinkles or the like, tends to be formed different from the pattern of the dermal layer, in some cases, orthogonal thereto. That is to say, with such a method, the epidermal pattern having poor stability is detected, leading to problem of poor precision of authentication.

On the other hand, with an arrangement according to the present invention, the epidermal pattern is not detected, but the structure of the tissue beneath the epidermis (e.g., the roughness pattern of the dermal layer) is detected by measuring electrostatic capacitance as described above, thereby solving all the aforementioned problems.

That is to say, with the present invention, biometric authentication is performed by detecting the structure of the tissue beneath the epidermis, and accordingly, the "biometric authentication" and the "living-tissue discrimination" are integrated. Accordingly, the system can discriminate and reject the tissue cut off from the body of the user by detecting absence of blood flow even if the tissue is alive by soaking in a physiological salt solution. Furthermore, the tissue which is to be authenticated needs to exhibit normal pulmonary circulation, normal heart beat, normal blood flow, and normal hemoglobin ratio in blood. Accordingly, if other persons cut off the arm of the user with a surgical method for "spoofing", there is the need to connect the blood vessels of the arm to a heart-lung machine, and to precisely reproduce the heat-beat wave. Accordingly, it is difficult to make "spoofing" in the current situation wherein mobile heart-lung machines are unavailable. If the mobile heart-lung machine becomes available in the future, such "spoofing" would require advanced surgical techniques and surgical equipment for performing: cutting off of the arm from the body; connection of the blood vessels of the arm to a heart-lung machine; treatment for fine blood vessels and nerves; prevention of change in the tissue due to vital reaction caused due to cutting off of the arm; stabilization of the tissue after resumption of blood flow; and so forth, which is far from practical. On the other hand, it is more difficult to create a forgery of the tissue having precisely the same three-dimensional structure of fine blood capillaries which causes the same scattering of the light, instead of the tissue cut of from the body of the user.

Furthermore, the present invention may be applied to a wearable arrangement. For example, an arrangement may be made wherein a wearable information device or a mobile information device includes detecting means for detecting the pattern of tissue, blood vessels, or the like, beneath the epidermis wherein visual observation is difficult under natural light, on the face thereof for being in contact with the skin of the user at the time of the user holding or wearing the information device, the skin-tissue pattern beneath the epidermis on the contact face between the body of the user and the information device is detected at the time of the user holding or wearing the information device, the detected pattern is compared to the patterns which have been registered in the information device or a server computer connected to the information device via network, thereby enabling the system to permit or restrict at least a part of the service provided from the information device or the network system based upon the detection results, i.e., thereby enabling so-called "access control".

Let us consider that the present invention is applied to a wearable authentication device such as wristwatch-type authentication device, or the like, for example. In this case, there is the need to strictly fix the position and the direction of the authentication device at the time of being fit by the user. Furthermore, the authentication device needs to be closely fit to the body of the user without looseness so as not to be deviated from the fitting position even if the user moves. Specifically, the system needs to determine the portion of the skin which is to be authenticated. On the other hand, an arrangement may be made wherein the interference pattern is registered for a wide skin region including the target region. However, such an arrangement requires pattern matching processing for searching the aforementioned wide region for a matched pattern, leading to a great processing load. Such a great load is undesirable for a mobile authentication device from the perspective of power consumption and so forth.

For example, let us consider a special case of the biometric authentication using the skin pattern, such as fingerprints or the like. In this case, the center of a whirl-shaped pattern, a horseshoe-shaped pattern, or the like, can be easily detected, and furthermore, the area of the surface of the finger having such a structure is narrow, thereby facilitating search for the position which is to be authenticated. However, other ordinary portions have relatively large area as compared with the fingertip, and have fine skin pattern having no geometric structure which facilitates search for the position which is to be authenticated, unlike the whirl-shaped pattern of the fingerprints, except for limited special portions, leading to extreme difficulty in search for the region which is to be authenticated.

In order to solve the aforementioned problem, an arrangement may be made wherein the skin pattern is registered for a wide region beforehand as described above, and the system determines whether or not the pattern detected at the time of authentication is included in the aforementioned registered pattern. However, such an arrangement leads to registration for an excessively large area, which is troublesome, and leads to a problem of excessive processing load and excessive processing period of time of the authentication device at the time of authentication. With an ideal arrangement, the skin pattern is preferably registered for the whole body. However, such an arrangement is not undesirable from the practical perspective as described above. Furthermore, in this case, it is difficult to determine the "wide region". In practical situations, the authentication device may deviate from the region at the time of authentication due to flexibility of the human body, or difference in the position to which the authentication device is fit for each authentication.

In order to solve the aforementioned problems, the skin containing a fork structure of the subcutaneous blood vessel is preferably used as the skin which is to be authenticated. The direction of the aforementioned principal axis can be easily obtained using the fork structure. For example, an arrangement may be made wherein the positional relation regarding the fork structure is determined and stored beforehand at the time of user registration, thereby enabling adjustment of the portion of the skin which is to be authenticated at the time of user authentication based upon the position of the blood-vessel fork structure in a simple manner.

[Method Using Temperature Difference]

Next, description will be made regarding detection of the tissue pattern and authentication using temperature difference. The skin structure comprises the epidermal tissue which has no blood vessels and is passive to the body temperature, and the dermal tissue which has blood vessels and actively affects the temperature through blood flow. This causes a relatively high temperature in the dermal tissue as compared with the epidermal tissue, except for special situations wherein heat is externally applied, such as exposure of direct sunlight to the body surface. A detecting device according to the present embodiment detects the structure of tissue beneath the epidermis using the aforementioned mechanism.

For example, the detecting device according to the present embodiment has a configuration wherein fine devices for detecting temperature such as thermistor bolometers, thermopiles, or the like, are two-dimensionally arrayed instead of the fine electrodes described above, and temperature is measured at each point. In this case, difference in temperature is detected between the fine devices corresponding to the thickness of the epidermal layer or the like underneath each fine device. The detecting device according to the present embodiment detects the roughness structure of the dermal layer beneath the epidermis using the aforementioned mechanism. In particular, thermopiles having a sensitive range corresponding to infrared light emitted from the human body are preferably employed as the fine devices for detecting temperature, thereby enabling detection while preventing adverse effects due to an external heat source such as sunlight or the like.

Furthermore, an arrangement may be made wherein infrared-light detecting means, which is a temperature detecting means, are disposed in the form of a matrix, and the detecting face thus formed is positioned close to the surface of the skin, thereby detecting the dermal layer pattern beneath the epidermal tissue, using the fact that the living tissue emits infrared light with a unique wavelength (e.g., wavelength of around 10 μm) due to the body temperature. With the present arrangement, a difference in the infrared magnitude is detected between the infrared detecting sensor units forming the matrix-shaped infrared detecting means, corresponding to the thickness of the epidermis or the distance between the sensor unit and the dermis serving as an infrared source. The detecting device according to the present arrangement detects the structure of the subcutaneous tissue, e.g., the roughness pattern of the dermal layer, based upon the infrared magnitude distribution.

Furthermore, an arrangement may be made wherein the positions of the blood vessels are detected using the fact that a portion containing the subcutaneous blood vessels exhibits a relatively high temperature as compared with the other portions, thereby enabling biometric authentication. Furthermore, an arrangement may be made wherein the position or the direction of the portion which is to be authenticated is determined based upon a detected image of blood capillaries. Furthermore, living-tissue discrimination may be performed based upon a detected image of blood capillaries, as well.

INDUSTRIAL APPLICABILITY

As can be clearly understood from the above description, the present invention enables ubiquitous biometric authentication using not only a special portion such as the fingertip or the like, but also any desired portion of the skin of the user. Furthermore, such a portion which is to be authenticated cannot be observed from the outside, unlike the fingerprints, and accordingly, it is difficult for other persons to identify the portion of the user body which is used for authentication. Thus, the present invention has the advantage of high security of privacy, as well as the advantage of high security against forgery.

Furthermore, the present invention provides an authentication method using the portion having active blood flow or active circulation of body fluid, such as the dermal tissue. The properties of such a portion exhibits high sensitivity to change in the blood flow or circulation of body fluid, thereby providing essential and complete integration of biometric authentication means and living-tissue discrimination. Thus, the present invention provides biometric authentication while suppressing the risk of surgical hazard, i.e., improving safety of the user.

Furthermore, the present invention may be applied to a wearable detecting device and a wearable authentication device having a detecting portion for being in contact with the skin of the human body, thereby enabling biometric authentication using daily actions of the user without any special user operations. Furthermore, even in the event that detection error or authentication error occurs, retry processing is performed without any particular user operations, and is not troublesome.

The invention claimed is:

1. An apparatus, comprising:
   a light emitting unit configured to emit near-infrared source light toward biological tissue;
   an imaging sensor configured to detect an image of a blood vessel, which is generated by scattered light scattered at the tissue, the imaging sensor further configured to convert the image to an electrical signal; and
   circuitry configured to detect a change in absorbance of the source light in blood in the tissue based on the electrical signal via obtaining a change in frequency between incident light and the scattered light as beat signals by detecting an interference between the incident light and the scattered light,
   wherein the change in the absorbance of the source light in the blood corresponds to a heart beat, and
   wherein the circuitry determines whether there is an absence of blood flow based on the detected change in the absorbance of the source light in the blood.

2. The apparatus of claim 1, wherein the absorbance of the source light in the blood is detected at a wavelength of 940 nm.

3. The apparatus of claim 1, wherein the absorbance of the source light in the blood is detected at a wavelength of 660 nm.

4. The apparatus of claim 1, further comprising an imaging optical system including
the imaging sensor, which receives light, and
an imaging lens set,
wherein the source light is cast at a slant toward the tissue.

5. The apparatus of claim 1, wherein the circuitry detects the change in the absorbance of the source light in the blood in a blood vessel.

6. The apparatus of claim 1, wherein the change in absorbance of the source light in blood in the tissue is determined by a pulse wave.

7. The apparatus of claim 1, wherein the change in absorbance of the source light in blood in the tissue is determined by an oxygen saturation level.

8. The apparatus of claim 1, wherein the circuitry detects change in the absorbance of the source light in hemoglobin in the blood.

9. The apparatus of claim 8, wherein the circuitry determines whether the hemoglobin is oxidized or deoxidized.

10. The apparatus of claim 1, wherein the circuitry further detects a hemoglobin ratio in the blood.

11. The apparatus of claim 1, wherein the change in absorbance of the source light in blood in the tissue is determined by one of a pulse wave, an oxygen saturation level.

12. An apparatus, comprising:
a non-transitory computer-readable storage medium including computer executable instructions, where the instructions, when executed by a processor, cause the processor to emit near-infrared source light toward biological tissue, and to detect a change in absorbance of the source light in blood in the tissue based on an electrical signal via obtaining a change in frequency between incident light and the scattered light as beat signals by detecting an interference between the incident light and the scattered light; and
an imaging sensor configured to detect an image of a blood vessel, which is generated by scattered light scattered at the tissue, the imaging sensor further configured to convert the image to the electrical signal,
wherein the change in the absorbance of the source light in the blood corresponds to a heart beat, and
wherein the processor determines whether there is an absence of blood flow based on the detected change in the absorbance of the source light in the blood.

13. A method comprising:
emitting near-infrared source light toward biological tissue;
detecting an image of a blood vessel, which is generated by scattered light scattered at the tissue;
converting the image to an electrical signal;
detecting a change in absorbance of the source light in blood in the tissue based on the electrical signal via obtaining a change in frequency between incident light and the scattered light as beat signals by detecting an interference between the incident light and the scattered light;
corresponding the change in the absorbance of the source light in the blood to a heart beat; and
determining whether there is an absence of blood flow based on the detected change in the absorbance of the source light in the blood.

14. The method of claim 13, wherein the detecting the change in the absorbance of the source light in the blood is detected in a blood vessel.

15. An information processing apparatus, comprising:
circuitry configured to detect a change in absorbance of a source light in blood in a tissue based on an electrical signal via obtaining a change in frequency between incident light and the scattered light as beat signals by detecting an interference between the incident light and the scattered light,
wherein the change in the absorbance of the source light in the blood corresponds to a heart beat, and
wherein the circuitry determines whether there is an absence of blood flow based on the detected change in the absorbance of the source light in the blood.

16. A system, comprising:
a light emitting unit configured to emit near-infrared source light toward biological tissue;
an imaging sensor configured to detect an image of a blood vessel, which is generated by scattered light scattered at the tissue, the imaging sensor further configured to convert the image to an electrical signal; and
the information processing apparatus according to claim 15.

17. The information processing apparatus of claim 15, wherein the absorbance of the source light in the blood is detected at a wavelength of one of 660 nm and 940 nm.

18. The information processing apparatus of claim 15, wherein the circuitry detects the change in the absorbance of the source light in the blood in a blood vessel.

* * * * *